(12) United States Patent
Tal

(10) Patent No.: US 11,123,518 B2
(45) Date of Patent: Sep. 21, 2021

(54) DUAL-TIP HEMODIALYSIS CATHETER

(71) Applicant: Pristine Access Technologies Ltd, Tel Aviv (IL)

(72) Inventor: Michael Gabriel Tal, Savyon (IL)

(73) Assignee: Pristine Access Technologies, LTD., Tel-Aviv (IL)

( * ) Notice: Subject to any disclaimer, the term of this patent is extended or adjusted under 35 U.S.C. 154(b) by 432 days.

(21) Appl. No.: 16/228,318

(22) Filed: Dec. 20, 2018

(65) Prior Publication Data

US 2019/0117935 A1   Apr. 25, 2019

Related U.S. Application Data

(63) Continuation of application No. 14/895,975, filed as application No. PCT/US2014/040935 on Jun. 4, 2014, now Pat. No. 10,363,390.

(Continued)

(51) Int. Cl.
*A61M 25/00* (2006.01)
*A61M 1/36* (2006.01)
*A61M 25/01* (2006.01)
*A61M 1/28* (2006.01)
*B29C 67/00* (2017.01)
*B29L 31/00* (2006.01)

(52) U.S. Cl.
CPC .......... *A61M 25/003* (2013.01); *A61M 1/285* (2013.01); *A61M 1/3661* (2014.02); *A61M 25/001* (2013.01); *A61M 25/0029* (2013.01); *A61M 25/0194* (2013.01); *A61M 25/0071* (2013.01); *A61M 2025/0031* (2013.01); *A61M 2025/0034* (2013.01); *A61M 2025/0073* (2013.01); *A61M 2205/0216* (2013.01); *A61M 2210/125* (2013.01); *B29C 67/0022* (2013.01); *B29L 2031/7542* (2013.01)

(58) Field of Classification Search
CPC ............ A61M 1/3661; A61M 25/0071; A61M 2025/0031; A61M 2025/0034; A61M 25/001; A61M 2205/0216; A61M 2025/0073; A61M 1/285; A61M 25/003
See application file for complete search history.

(56) References Cited

U.S. PATENT DOCUMENTS 5,156,592 A   10/1992   Martin et al.
5,800,414 A    9/1998   Cazal
(Continued)

FOREIGN PATENT DOCUMENTS

CN   101918066 A   7/2013
EP   1610853 A1   1/2006
(Continued)

OTHER PUBLICATIONS

Dec. 17, 2014 International Search Report issued in International Patent Application No. PCT/US2014/040935.
(Continued)

*Primary Examiner* — Leslie R Deak
(74) *Attorney, Agent, or Firm* — Rutan & Tucker LLP

(57) ABSTRACT

A dual tip dialysis catheter has a proximal portion with connected lumens and a distal portion with diverging lumens. The lumens may separate at a split junction and diverge in a scissors like manner to reduce or eliminate a crack or gap adjacent to the split junction, thereby reducing clotting. A dual tip dialysis catheter may have forward openings configured to direct flow in opposite directions.

24 Claims, 13 Drawing Sheets

Related U.S. Application Data

(60) Provisional application No. 61/939,158, filed on Feb. 12, 2014, provisional application No. 61/831,024, filed on Jun. 4, 2013.

(56) References Cited

U.S. PATENT DOCUMENTS

| | | |
|---|---|---|
| 5,947,953 A | 9/1999 | Ash et al. |
| 6,001,079 A | 12/1999 | Pourchez |
| 6,482,169 B1 | 11/2002 | Kuhle |
| 6,513,527 B1 | 2/2003 | Abdel-Aziz |
| 7,108,674 B2 | 9/2006 | Quinn |
| 7,182,746 B2 | 2/2007 | Haarala et al. |
| 7,776,005 B2 | 8/2010 | Haggstrom et al. |
| 8,066,660 B2 | 11/2011 | Gregersen et al. |
| 8,092,415 B2 | 1/2012 | Moehle et al. |
| 2002/0052641 A1 | 5/2002 | Monroe et al. |
| 2002/0062129 A1 | 5/2002 | Mikus et al. |
| 2003/0153898 A1 | 8/2003 | Schon et al. |
| 2004/0092863 A1 | 5/2004 | Raulerson et al. |
| 2004/0167463 A1 | 8/2004 | Zawacki et al. |
| 2005/0054989 A1 | 3/2005 | McGuckin et al. |
| 2005/0277862 A1 | 12/2005 | Anand |
| 2006/0025781 A1 | 2/2006 | Young et al. |
| 2006/0149350 A1 | 7/2006 | Patel et al. |
| 2007/0208276 A1 | 9/2007 | Volk et al. |
| 2007/0225661 A1 | 9/2007 | Ash et al. |
| 2009/0137944 A1 | 5/2009 | Haarala et al. |
| 2009/0204052 A1 | 8/2009 | Nimkar et al. |
| 2009/0204079 A1 | 8/2009 | Nimkar et al. |
| 2009/0209940 A1 | 8/2009 | Nimkar et al. |
| 2011/0011525 A1 | 1/2011 | Sanscoucy |
| 2012/0130392 A1 | 5/2012 | Levy et al. |
| 2012/0143123 A1 | 6/2012 | Agnew |
| 2012/0179102 A1 | 7/2012 | Blanchard et al. |
| 2013/0324964 A1 | 12/2013 | Florescu |
| 2014/0261407 A1 | 9/2014 | Roberts et al. |

FOREIGN PATENT DOCUMENTS

| | | |
|---|---|---|
| EP | 1792637 A3 | 3/2008 |
| EP | 2277579 A1 | 1/2011 |
| EP | 2446915 B1 | 1/2018 |
| WO | 9115255 A1 | 10/1991 |
| WO | 1997009086 A1 | 3/1997 |
| WO | 2003045464 A2 | 6/2003 |

OTHER PUBLICATIONS

ISR received for PCT Application No. PCT/IB2016/054317, dated Nov. 15, 2016, 5 pages.

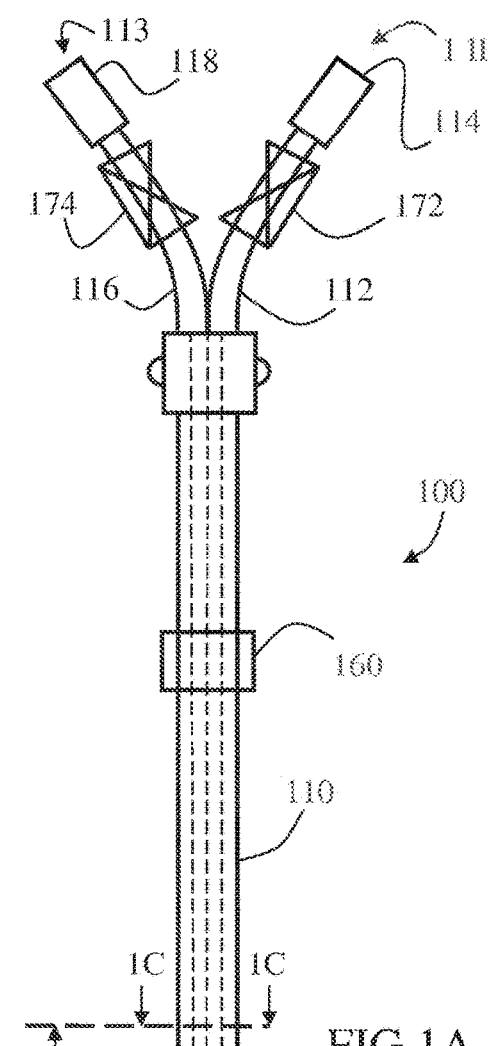
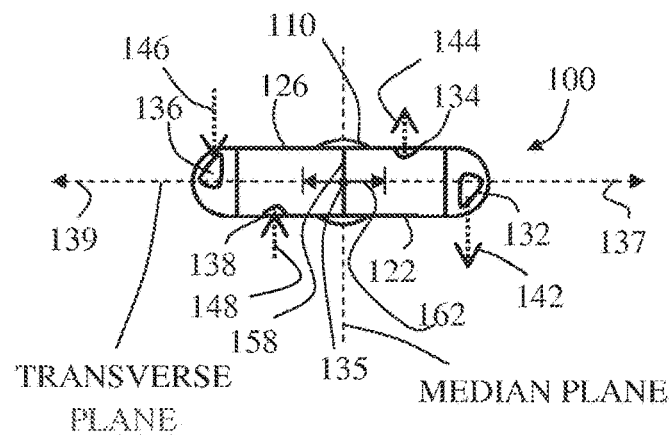
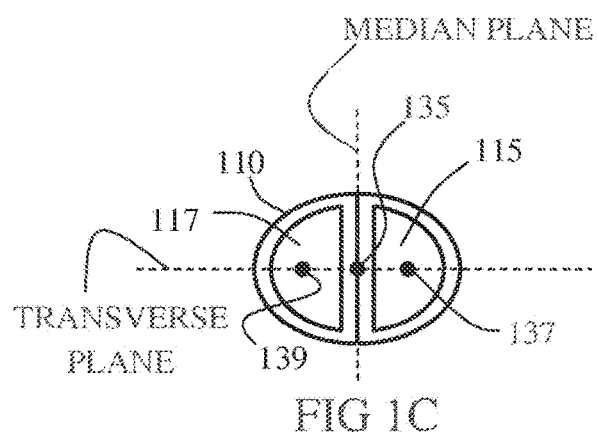
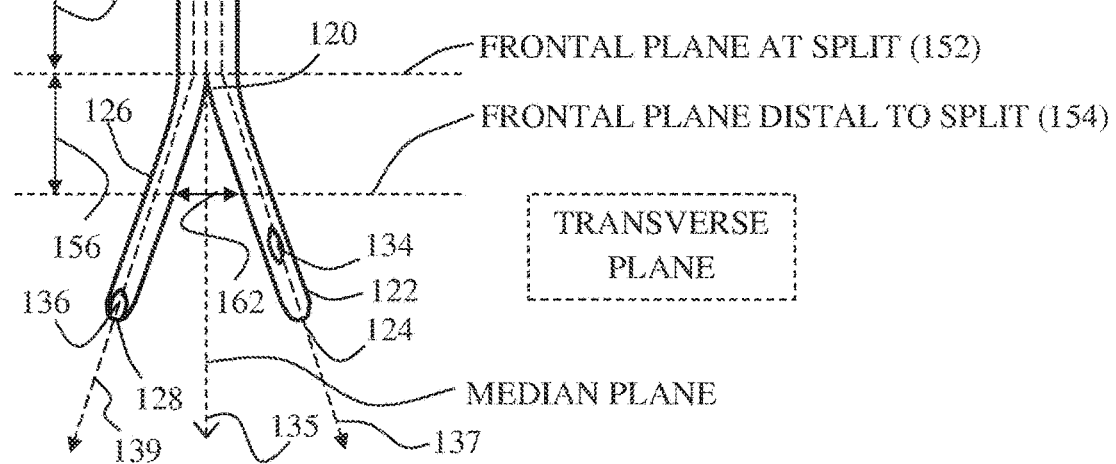
FIG 1A
FIG 1B
FIG 1C

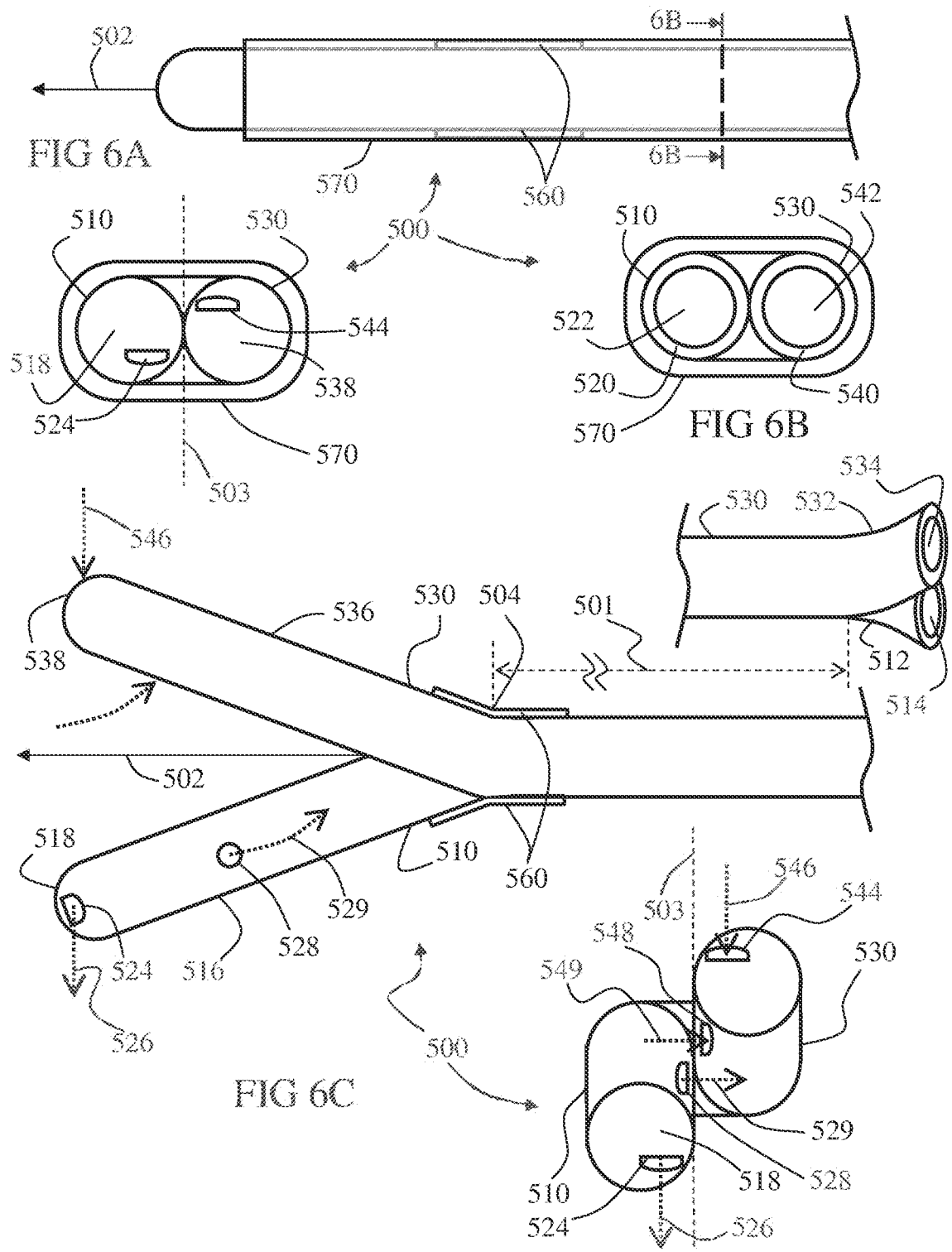

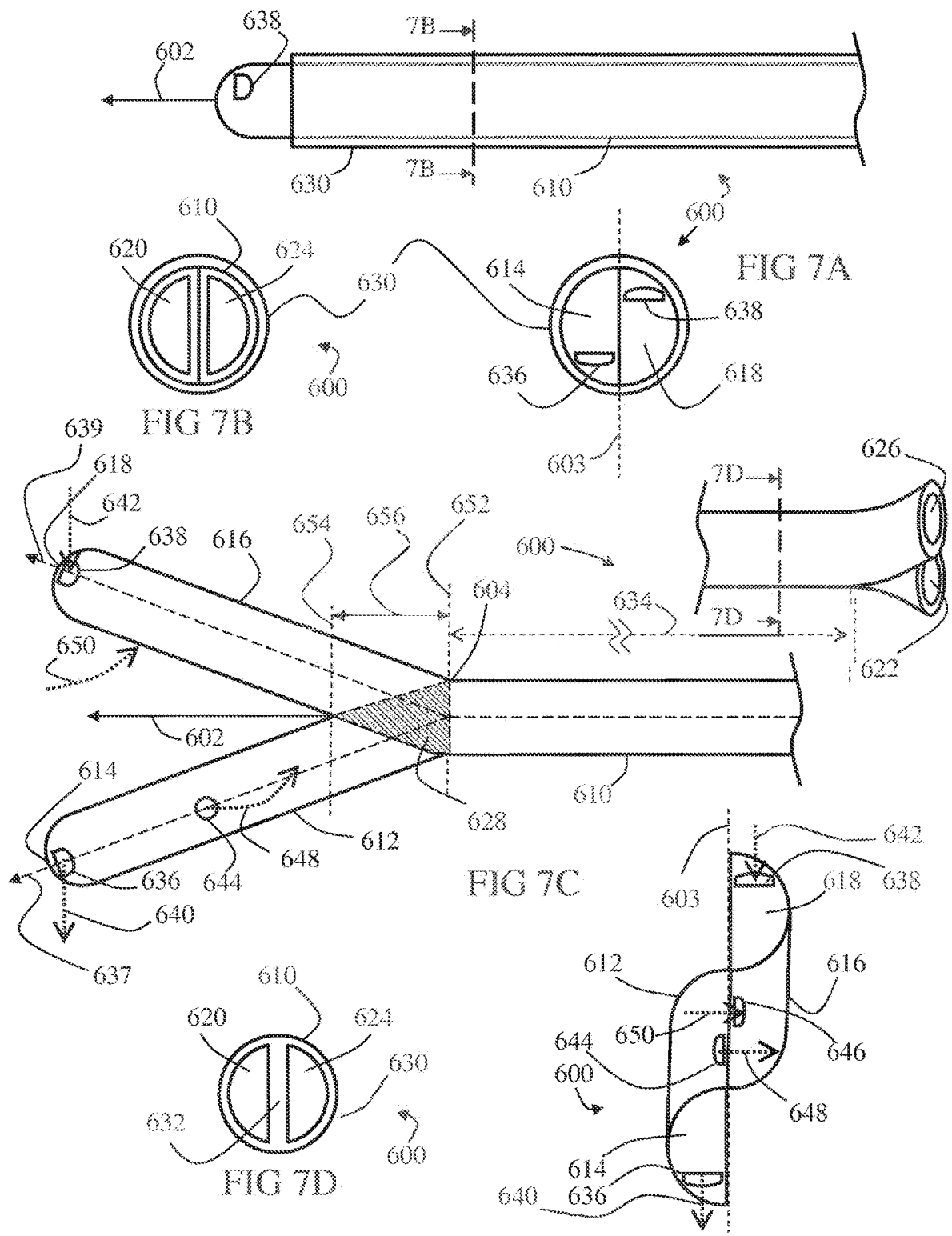

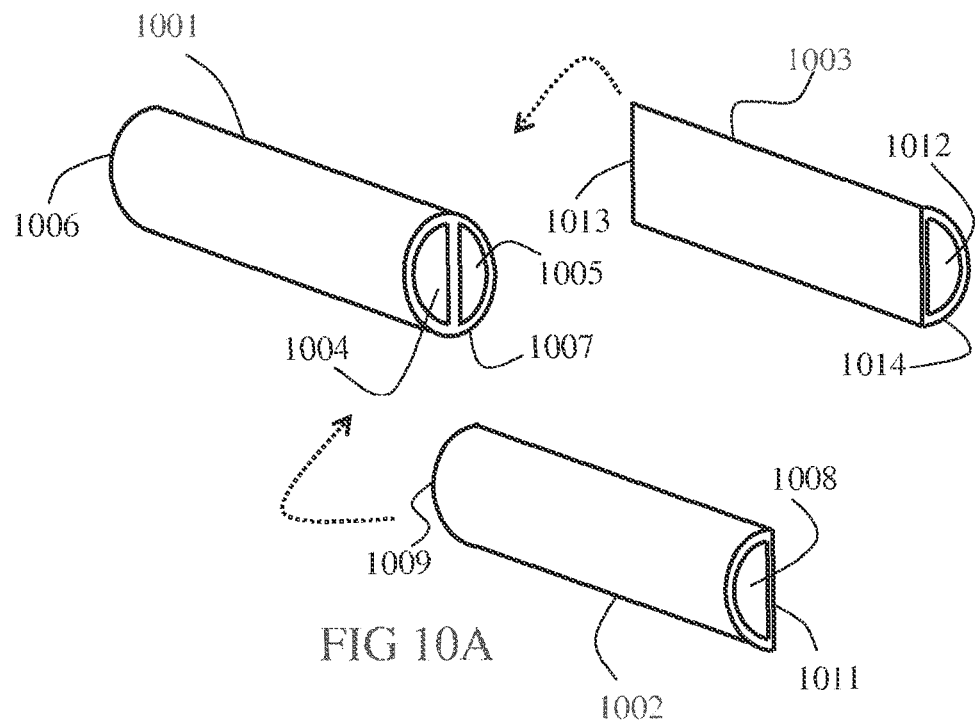
FIG 10A
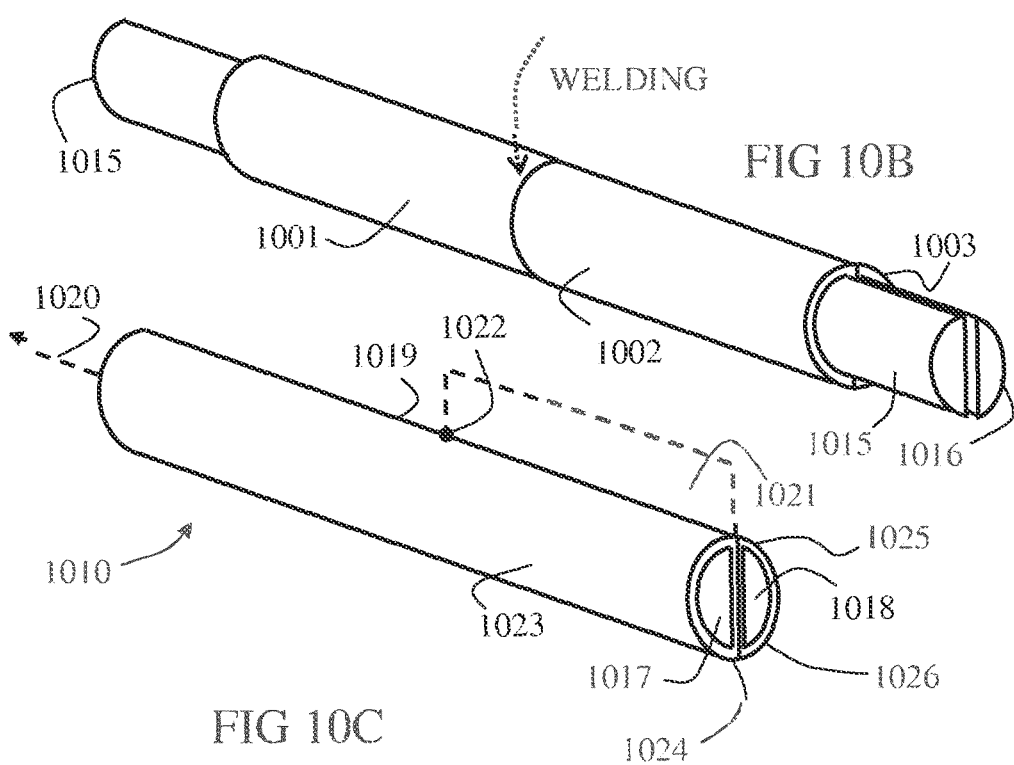
FIG 10B
FIG 10C

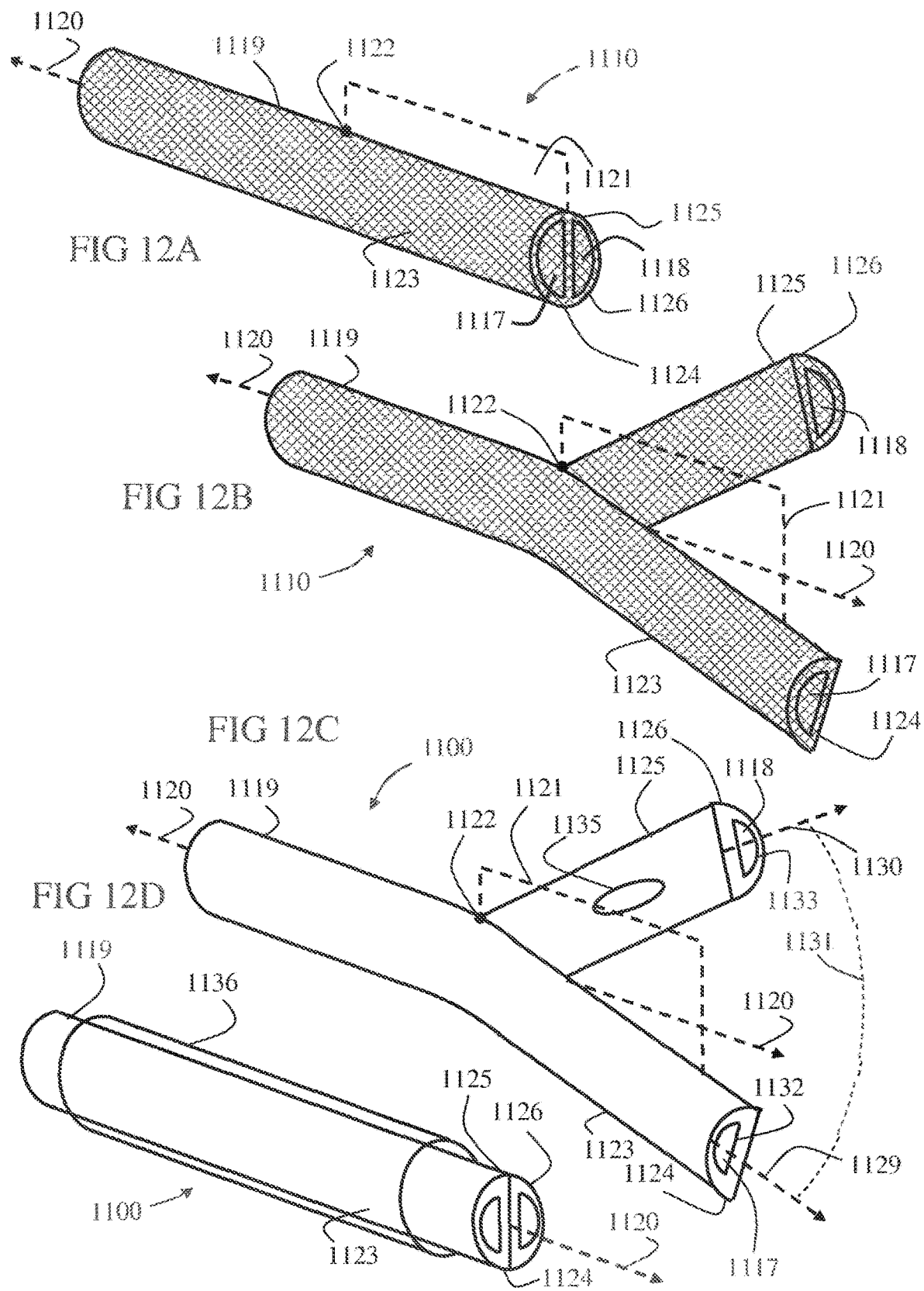

DUAL-TIP HEMODIALYSIS CATHETER

PRIORITY

This application is a continuation of U.S. patent application Ser. No. 14/895,975, filed Dec. 4, 2015, now U.S. Pat. No. 10,363,390, which is a U.S. national stage of International Application No. PCT/US2014/040935, filed Jun. 4, 2014, which claims priority to U.S. Provisional Application No. 61/939,158, filed Feb. 12, 2014, and to U.S. Provisional Application No. 61/831,024, filed Jun. 4, 2013, each of which is incorporated by reference in its entirety into this application.

FIELD AND BACKGROUND OF THE INVENTION

The present invention, in some embodiments thereof, relates to medical catheter apparatus and in particular to dialysis catheters having dual or split tip.

Split-tip dialysis catheters are mostly used in current days for chronic use of exchanging blood to and from the patient and the hemodialysis machine. During an exemplary hemodialysis procedure, a multiple lumen catheter is inserted into a body and blood is withdrawn through an arterial lumen of the catheter. This blood is supplied to a hemodialysis machine which dialyzes, or cleans, the blood to remove waste and excess water. The dialyzed blood is returned to the patient through a venous lumen of the catheter. Flow in the catheter may need to be reversed from time to time so that blood will flow in opposite direction in both arterial lumen and venous lumen to as mentioned above.

Some complications may occur in split tip catheters. At first, recirculation of blood flow is a known phenomenon in which the dialyzed blood exiting a catheter's lumen is directly returned to the other lumen without efficiently affecting surroundings. Another complication of hemodialysis catheters is flow occlusion. Flow occlusion is primarily caused by blockage of the arterial lumen. Common causes of occlusion are fibrin sheath formation, thrombus formation and positional occlusion. With positional occlusion of the catheter, there can be difficulty in removing blood from the patient. For example, a tip of the catheter has, to some extent, freedom of movement inside the patient, and this can cause occlusion, as a tip of the catheter or a side hole may be sucked against a blood vessel or heart wall.

In addition, split or dual tip dialysis catheters pose a unique feature in their current design, which makes them more prone to clotting complications. The area immediately below the separation zone of the two lumens (i.e., immediately distal to the junction) is a source of problem. With current known designs, in which the two lumens are separated directly away from each other, there is a dead space with slow and turbulent flow which makes this area very likely to form a clot. Those blood clots are a major complication of split tip dialysis catheters and are associated with increased morbidity.

The following Patent documents are believed to represent the current state of the art: U.S. Pat. Nos. 5,800,414; 5,947,953; 7,108,674; 7,182,746; 7,776,005; 8,066,660; and 8,092,415.

SUMMARY OF THE INVENTION

According to an aspect of some embodiments of the present invention there is provided a catheter assembly which comprises a first lumen having a first longitudinal axis extending along the center of the first lumen, and a second lumen having a second longitudinal axis extending along the center of the second lumen. In some embodiments, when the catheter is in a relaxed configuration the first and second longitudinal axes of the lumens are parallel over a proximal portion of the catheter and diverge over a distal portion of the catheter.

In some embodiments, the first and second longitudinal axes define a transverse plane that contains both the first and second longitudinal axes in the proximal portion of the catheter. Optionally, the first and second longitudinal axes further define a median plane parallel to and between the first and second longitudinal axes in the proximal portion of the catheter.

In some embodiments, over the distal portion of the catheter where the first and second longitudinal axes diverge, at least one of the first and second longitudinal axes diverges from the transverse plane when the catheter is in the relaxed configuration. Optionally, additionally or alternatively, over the distal portion of the catheter where the first and second longitudinal axes diverge from each other, the first longitudinal axis and the second longitudinal axis each remain approximately the same perpendicular distance from the median plane.

In some embodiments, in the relaxed configuration, the longitudinal axis of at least one of the first and second lumens diverges at least one centimeter away from the transverse plane at the tip of the diverging lumen. Optionally, in the relaxed configuration, the longitudinal axes of both of the first and second lumens diverge less than five millimeters farther away from the median plane at the tip of the diverging lumens.

In an aspect of some embodiments in accordance with the present disclosure, there is provided a catheter comprising a first lumen defined by a first lumen wall and a second lumen defined by a second lumen wall. In some embodiments, the catheter comprises a proximal portion where the first lumen wall and the second lumen wall are connected with each other to extend in parallel with each other, a distal portion where the first lumen wall and the second lumen wall are not parallel with each other when the catheter is in a relaxed configuration, and a junction portion where the first lumen wall and the second lumen wall contact each other, but the first lumen wall and the second lumen wall do not extend parallel to each other.

In an aspect of some embodiments in accordance with the present disclosure, there is provided a split tip dialysis catheter comprising an unsplit proximal portion, a split distal portion and a junction where the unsplit proximal portion splits to form the split distal portion. The catheter also includes a junction portion in the split distal portion and distal to the junction comprising a portion of the dialysis catheter having facing planar lumen walls. In some embodiments, the dihedral angle formed by the intersection of the planes defined by the facing planar lumen walls is less than 10 degrees when the catheter is in a relaxed configuration. In some embodiments, the dihedral angle is less than 5 degrees, optionally less than 1 degree. Optionally, no gap or crack greater than 0.5 mm is present in the junction portion. Optionally, the junction portion is the portion of the catheter extending 5 mm distal to the split, optionally 10 mm distal to the split, or optionally 20 mm distal to the split.

In an aspect of some embodiments in accordance with the present disclosure, there is provided a hemodialysis catheter, comprising an elongated body extendable along a longitudinal axis longitudinally split relative to a splitting plane at a junction into a first distal end region terminating in a first tip and a second distal end region terminating in a second tip. In some embodiments, the elongated body encloses a first lumen extending between a first proximal port and the first tip, and a second lumen extending between a second proximal port and the second tip. In some embodiments, the elongated body comprises an elastic portion or elastic member, about the junction, having a non-stressed form at the first end region and the second end region being separated with each other along the splitting plane with no gap therebetween adjacent the junction. In some embodiments, the first lumen and the second lumen are independent one to the other for facilitating simultaneous flow in opposite directions.

In some embodiments, the catheter includes removable aligning means aligning the first distal end region together with the second distal end region to the longitudinal axis, wherein upon removal thereof, the first distal end region and the second distal end region can voluntarily slide against each other, such as in a scissor-like movement, along the splitting plane, up to the non-stressed form of said elastic portion or elastic member. Optionally, the removable aligning means includes a removable cover such as a peel away sheath. Optionally, a septum divides the first lumen and the second lumen along a non-splitting length of the elongated body.

In some embodiments, the second tip is in apposition to the first tip when the first distal end region and the second distal end region are aligned. Optionally, the first distal end region and the second end region are formed in rotational symmetry one with the other relative to the longitudinal axis and comprising a plurality of openings distributed and shaped in accordance with the rotational symmetry. Optionally, each of the first distal end region and the second distal end region comprises at least two openings shaped to direct flow passing therethrough in different directions.

In some embodiments, the first distal end region comprises a first forward opening located adjacent to the first tip and the second distal end region comprises a second forward opening located adjacent to the second tip. Optionally, the first forward opening is shaped such to direct flow passing therethrough in a first course having a first direction and wherein the second forward opening is shaped such to direct flow passing therethrough in a second course nonintersecting with the first course. Optionally, the first distal end region comprises a first lateral opening located proximally to the first forward opening, and the second distal end region comprises a second lateral opening located proximally to the second forward opening. Optionally, the first lateral opening is shaped such to direct flow passing therethrough away from the first direction. Optionally, the second lateral opening is shaped such to direct flow passing therethrough in or towards the first direction. Optionally, the first lateral opening is shaped such to direct flow passing therethrough vertically to the first direction.

In some embodiments, the first course having an orthogonal projection parallel to the splitting plane. Optionally, the splitting plane is a median plane of the hemodialysis catheter. Optionally, the first course having an orthogonal projection parallel to a transverse plane orthogonal to the splitting plane in same Cartesian coordinate system. Optionally, the first course having an orthogonal projection parallel to a frontal plane orthogonal to the splitting plane in same Cartesian coordinate system.

According to an aspect of some embodiments of the present invention there is provided a catheter assembly, which includes a first catheter and a second catheter merged along a length includes a longitudinal assembly axis. In some embodiments, the first catheter has a first proximal end region includes a first port, a first distal end region terminating in a first tip, and a first wall defining a first lumen extending longitudinally therethrough between the first port and the first tip. Optionally and additionally, the second catheter has a second proximal end region includes a second port, a second distal end region terminating in a second tip in apposition to the first tip, and a second wall defining a second lumen extending longitudinally therethrough between the second port and the second tip. In some embodiments, the first wall and the second wall are longitudinally split from each other at a junction positioned at or proximally to the first and second distal end regions. Optionally, the first distal end region and the second end region are formed rotationally symmetric one with the other relative to the longitudinal assembly axis.

In some embodiments, the first catheter includes a first forward opening located at the first tip and the second catheter includes a second forward opening located at the second tip, wherein the first forward opening is shaped such to direct flow passing therethrough in a first direction and wherein the second forward opening is shaped such to direct flow passing therethrough in a second direction opposite to the first direction. In some embodiments, the first catheter includes a first lateral opening located at the first distal end region proximal to the first forward opening, and the second catheter includes a second lateral opening located at the second distal end region proximal to the second forward opening.

In some embodiments, the first catheter and/or the second catheter comprises an elastic portion or elastic member, about the junction, having a non-stressed form at the first end region and the second end region being separated with each other along the splitting plane with no gap therebetween adjacent the junction.

In some embodiments, the catheter assembly comprises removable aligning means aligning the first distal end region together with the second distal end region to the longitudinal assembly axis, wherein upon removal thereof, the first distal end region and the second distal end region can voluntarily slide against each other, such as in a scissor-like movement, along the splitting plane, up to the non-stressed form of the elastic portion or elastic member.

According to an aspect of some embodiments of the present invention there is provided a hemodialysis catheter, which comprises an elongated body extendable along a longitudinal assembly axis and splitting at a junction into a first distal end region terminating in a first tip and a second distal end region terminating in a second tip.

In some embodiments, the elongated body encloses a first lumen extending between a first proximal port and the first tip, and a second lumen extending between a second proximal port and the second tip.

In some embodiments, the first distal end region and the second end region are formed in rotational symmetry one with the other relative to the longitudinal assembly axis, and comprises a plurality of openings distributed and shaped in accordance with the rotational symmetry.

In some embodiments, the elongated body comprises an elastic portion or elastic member, about the junction, having a non-stressed form at the first end region and the second end region being separated with each other along the splitting plane with no gap therebetween adjacent the junction.

In some embodiments, the hemodialysis catheter comprises removable aligning means aligning the first distal end region together with the second distal end region to the longitudinal assembly axis, wherein upon removal thereof, the first distal end region and the second distal end region can voluntarily slide against each other, such as in a scissor-like movement, along the splitting plane, up to the non-stressed form of the elastic portion or elastic member.

In an aspect of some embodiments in accordance with the present disclosure there is provided a method for forming a dual-tip catheter, which comprises at least one of the following steps (not necessarily in same order):

a. providing a preformed part of the catheter comprising an elongated body, extendable along a longitudinal axis, longitudinally split relative to a splitting plane at a junction into a first distal end region terminating in a first tip and a second distal end region terminating in a second tip, wherein the elongated body encloses a first passage extending along the longitudinal axis and opened at the first tip, and a second passage extending along the longitudinal axis and opened at the second tip;

b. inserting a first contoured mandrel in the first passage and a second contoured mandrel in the second passage, such that the first end region is held in a first contour imposed by the first contoured mandrel and the second end region is held in a second contour imposed by the second contoured mandrel;

c. treating the elongated body thereby relieving internal stresses thereof; and d. removing the first contoured mandrel from the first passage and the second contoured mandrel from the second passage, wherein the elongated body in a non-stressed form thereof has the first end region and the second end region separated with each other along the splitting plane with no gap therebetween adjacent the junction.

In some embodiments, each of the first contoured mandrel and the second contoured mandrel is fixedly angled or curved along length thereof. Optionally, the first contoured mandrel is congruent, or geometrically similar about corresponding angles or curvatures thereof, to the second contoured mandrel.

In some embodiments, the elongated body in a non-stressed form thereof has the first tip pointed towards a first direction and the second tip pointed towards a second direction angled to the first direction relative to the splitting plane. Optionally, both the first direction and the second form straight lines with the junction forming a plane angle therebetween in the splitting plane.

In some embodiments, the first end region held in the first contour and the second end region held in the second contour form rotational symmetry one with the other relative to the longitudinal axis. Optionally, each of the first distal end region and the second distal end region comprises at least one opening distributed and shaped in accordance with the rotational symmetry. Optionally, each of the first distal end region and the second distal end region comprises at least two openings shaped to direct flow passing therethrough in different directions. Optionally, the first distal end region comprises a first forward opening located adjacent to the first tip and the second distal end region comprises a second forward opening located adjacent to the second tip, wherein the first forward opening is shaped such to direct flow passing therethrough in a first course nonintersecting with a flow in a second course directed by the second forward opening. Optionally, the first distal end region comprises a first lateral opening located proximally to the first forward opening, and the second distal end region comprises a second lateral opening located proximally to the second forward opening.

In some embodiments, the method of forming the catheter further includes a step of heating the elongated body, such that the first passage is shaped in accordance with outer boundaries of the first contoured mandrel and the second passage is shaped in accordance with outer boundaries of the second contoured mandrel.

In some embodiments, the elongated body comprises an elastic portion or elastic member, across the junction. Optionally, the method of forming the catheter also includes a step of coupling removable aligning means for aligning the first distal end region together with the second distal end region to the longitudinal axis. In some embodiments, upon removal of the aligning means, the first distal end region and the second distal end region can voluntarily slide against each other, such as in a scissor-like movement, along the splitting plane, up to the non-stressed form. Optionally, the removable aligning means includes a removable cover such as a peel away sheath.

In some embodiments, the second tip is in apposition to the first tip when the first distal end region and the second distal end region are aligned.

In some embodiments, the elongated body is formed of a fluid sealed material whereby the first passage forms a first lumen and the second passage forms a second lumen sealed to the first lumen. Optionally, a septum divides the first lumen and the second lumen along a non-splitting length of the elongated body. Optionally, the fluid sealed material includes at least one of silicone rubber, polyurethane, polycarbonate-based thermoplastic polyurethanes and Carbothane.

In some embodiments, the preformed part is formed by at least one of the following steps (not necessarily in same order):

I. collecting a first preformed member, a second preformed member and a third preformed member, wherein the first preformed member encloses a plurality of lumens extending therealong and opened at both ends thereof, the second preformed member encloses one lumen extending therealong and opened at both ends thereof, and the third preformed member encloses one lumen extending therealong and opened at both ends thereof;

II. welding the second preformed member and the third preformed member to the first preformed member to form the elongated body, whereby one lumen of the first preformed member and the one lumen of the second preformed member forms the first passage, and other lumen of the first preformed member and the one lumen of the third preformed member forms the second passage;

III. inserting a first straight mandrel through the one lumen of the first preformed member and the one lumen of the second preformed member and a second straight mandrel through the other lumen of the first preformed member and the one lumen of the third preformed member; and IV. aligning and/or approximating the first, second and third preformed members over the first and second straight mandrels; and V. heating the first, second and/or third preformed members, or the welded elongated body, such that the first passage is shaped in accordance with outer boundaries of the first straight mandrel and the second passage is shaped in accordance with outer boundaries of the second straight mandrel.

In some embodiments, the preformed part is formed of a meshed structure. Optionally, the meshed structure comprises at least one helically wound filament. Optionally, the filament is made from metal, polymer, carbon and/or glass. In some embodiments, the method includes impregnating and/or coating the preformed part with a polymeric solution.

In some embodiments, treating the elongated body includes at least one of heat treatment, chemical treatment, hardening, and plastic deformation.

In some embodiments, treating the elongated body creates elastic resistivity to a deviation from the non-stressed form.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-C schematically illustrate an exemplary dual-tip hemodialysis catheter assembly, in accordance with embodiments of the present invention;

FIGS. 6A-C schematically illustrate a catheter assembly, comprising a first catheter and a second catheter merged along a length comprising a longitudinal assembly axis, in accordance with embodiments of the present invention;

FIGS. 7A-D schematically illustrate a hemodialysis catheter, comprising an elongated body extendable along a longitudinal assembly axis and longitudinally split from each other, in accordance with embodiments of the present invention;

FIGS. 10A-G schematically illustrate different scenarios representing possible exemplary steps in a method for forming a dual-tip catheter, in accordance with embodiments of the present invention;

FIGS. 12A-D schematically illustrate different scenarios representing possible exemplary steps in another method for forming a dual-tip catheter, in accordance with embodiments of the present invention.

DESCRIPTION OF EMBODIMENTS OF THE INVENTION

Figure 2:
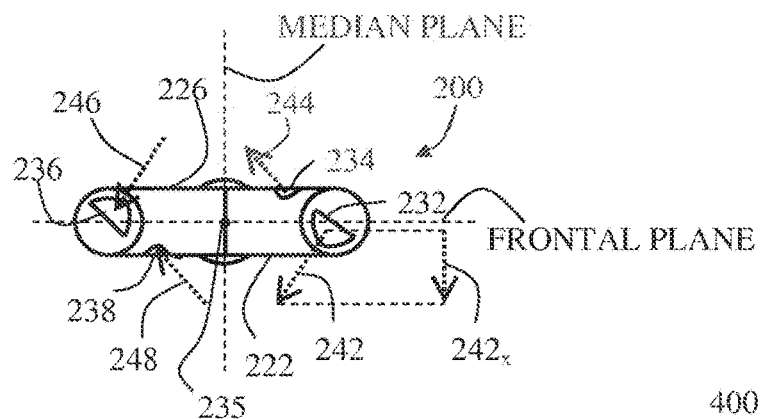
FIG. 2 schematically illustrates an exemplary dual-tip hemodialysis catheter assembly with partially facing distal openings, in accordance with embodiments of the present invention.

The following preferred embodiments may be described in the context of exemplary dialysis procedures for ease of description and understanding. However, the invention is not limited to the specifically described devices and methods, and may be adapted to various clinical applications without departing from the overall scope of the invention.

The present invention, in some embodiments thereof, relates to medical catheter apparatus and in particular to dialysis catheters having dual tip.

An aspect of some embodiments of the present invention relates to a catheter assembly, comprising a first catheter and a second catheter. In some embodiments, the catheter assembly is intended for hemodialysis process and is connectable to a hemodialysis machine wherein one catheter is set to deliver oxygenated blood into the cardiovascular system and the other catheter is set to draw blood therefrom, and optionally occasionally reverse the blood circulation between these two catheters. In some embodiments, the first catheter and the second catheter are merged along a length comprising a longitudinal assembly axis, optionally until a distal splitting point/line and/or in-between a distal splitting point/line and a proximal splitting point/line.

In some embodiments, the first catheter has a first proximal end region including a first port, a first distal end region terminating in a first tip, and a first wall defining a first lumen extending longitudinally therethrough between the first port and the first tip. Optionally and additionally, the second catheter has a second proximal end region including a second port, a second distal end region terminating in a second tip, and a second wall defining a second lumen extending longitudinally therethrough between the second port and the second tip. In some embodiments, the first lumen and the second lumen are independent from each other for facilitating simultaneous flow in opposite directions. In some embodiments, the first wall and the second wall are longitudinally split from each other, optionally relative to a median plane at a splitting line or a junction positioned at or proximally to the first and second distal end regions. Optionally, the first distal end region of the first catheter and the second distal end region of the second catheter extend substantially the same from the splitting line or junction such that the second tip is in apposition to the first tip.

In some embodiments, a catheter assembly comprises a first lumen having a first longitudinal axis extending along the center of the first lumen and a second lumen having a second longitudinal axis extending along the center of the second lumen. When the catheter assembly is in a relaxed configuration the first and second longitudinal axes of the lumens are parallel over a proximal portion of the catheter and diverge over a distal portion of the catheter. The first and second longitudinal axes define a transverse plane that contains both the first and second longitudinal axes in the proximal portion of the catheter. The first and second longitudinal axes further define a median plane parallel to and between the first and second longitudinal axes in the intermediate portion of the catheter. Over the distal portion of the catheter where the first and second longitudinal axes diverge, at least one of the first and second longitudinal axes diverges from the transverse plane when the catheter is in the relaxed configuration.

In some embodiments, a catheter comprises a first lumen defined by a first lumen wall, a second lumen defined by a second lumen wall, a proximal portion where the first lumen wall and the second lumen wall are connected with each other to extend in parallel with each other, a distal portion where the first lumen wall and the second lumen wall are not in contact with each other such that when the catheter is in a relaxed configuration the first and second lumens diverge from each other, and an intermediate portion between the proximal portion and the distal portion where the first lumen wall and the second lumen wall contact each other, but the first lumen wall and the second lumen wall do not extend parallel to each other.

In some embodiments, a split tip dialysis catheter comprises a split distal portion, an unsplit proximal portion, and a crack-free junction between the split distal portion and the unsplit proximal portion when the catheter is in a relaxed configuration.

The first distal end region and the second end region may be substantially pliant to juxtaposingly conform to boundaries of a hosting vessel lumen. Optionally and alternatively, the first distal end region and the second end region are substantially elastic or rigid such that the first distal tip and the second distal tip are provided in a predetermined distance and/or relative positioning upon deployment. In some embodiments, the first distal end region and the second end region are rotationally symmetric one with the other relatively to the longitudinal assembly axis, optionally distanced similarly about a transverse plane (relatively to the median plane) and/or optionally distanced similarly about the median plane (relatively to the transverse plane). Rotational symmetry may include only the general shape and optionally contouring of the end regions or may also include openings number, size, shape and/or distribution between the end regions in rotational symmetry.

In some embodiments, the first catheter includes a first forward opening located at the first distal tip and the second catheter includes a second forward opening located at the second distal tip. Optionally, the first forward opening is shaped such to direct flow passing therethrough in a first direction having a Cartesian component parallel to the median plane and the second forward opening is shaped such to direct flow passing therethrough in a second direction opposite to the first direction.

In some embodiments, the first catheter includes a first lateral opening located at the first distal end region proximal to the first forward opening, and the second catheter includes a second lateral opening located at the second distal end region proximal to the second forward opening.

In some embodiments, the first lateral opening is shaped such to direct flow passing therethrough in opposite direction to the first direction and/or the second lateral opening is shaped such to direct flow passing therethrough in opposite direction to the second direction. Optionally and alternatively, the first lateral opening is shaped such to direct flow passing therethrough in same direction as the first direction and/or the second lateral opening is shaped such to direct flow passing therethrough in same direction as the second direction. Optionally and alternatively, the first lateral opening is shaped such to direct flow passing therethrough vertically to the first direction and/or the second lateral opening is shaped such to direct flow passing therethrough vertically to the second direction.

Referring now to the drawings, FIGS. 1A-C schematically illustrate an exemplary dual-tip hemodialysis catheter assembly 100, in accordance with embodiments of the present invention. Set forth below are a variety of descriptions of the geometric configuration of the distal portions of catheters. As catheters are made of flexible material, they can of course be pushed, pulled, or stretched into a wide variety of configurations. Unless otherwise specified, such as describing a catheter in a sheath, the geometric configurations described herein are the configurations that the subject catheter naturally takes due to its inherent construction and material properties when the distal portion is in a "relaxed" or "non-stressed" state. FIGS. 1A and 1B illustrate the catheter in a "relaxed" or "non-stressed" configuration. The catheter is in a relaxed or non-stressed configuration when hanging freely downward as illustrated in FIG. 1A, being held or supported in the proximal region (such as region 159) with the distal portion that extends downward to the tips being free of external forces. As shown in FIG. 1, split or dual tip catheters typically have relaxed configurations where the walls forming individual lumens diverge from each other in the distal region of the catheter assembly.

Catheter assembly 100 includes an elongated body 110 merging a first catheter 111 forming walls enclosing a first lumen 115 and a second catheter 113 forming walls enclosing a second lumen 117 that is isolated from first lumen 115. Each lumen 115, 117 defines a longitudinal axis 137, 139 respectively, centrally located within and extending along the length of each lumen. The catheter assembly 100 further defines an assembly longitudinal axis 135 centrally located in the elongated body. Although the term "centrally located" should be clear to those in the art, for absence of doubt, for each lumen this means at the centroid of the cross sectional shape perpendicular to lumen extent (such as shown in FIG. 1C) as defined by the inner surface of the walls forming each lumen. For the catheter assembly as a whole this means at the centroid of the cross sectional shape perpendicular to lumen extent (such as shown in FIG. 1C) as defined by the outer surface of the elongated body 110. Optionally and as illustrated schematically, the catheters are merged along the longitudinal axis 135 up to a splitting point or line 120, also referred to herein as the junction. This point defines the location of a frontal plane 152 at the split or junction 120 that is perpendicular to the extent of the elongated body 110 at the point of the split 120. If the splitting line has a longitudinal extent, the position of the junction 120, and thus the frontal plane 152, is considered to be the proximal initiation point of the split.

The portion of the catheter assembly proximal to and within 2 cm of the frontal plane 152 is referred to as the connected or merged portion of the catheter assembly (designated 159 in FIG. 1A). In the connected or merged portion, the lumens extend parallel to each other. The portion of the catheter assembly distal to the frontal plane 152 to the most distal tip of the catheter assembly is referred to as the dual or split portion of the catheter assembly. In this split portion, the longitudinal axes of the lumens diverge from each other.

To facilitate explanation of the structure of some embodiments described herein, also defined in FIG. 1 is a frontal plane 154 distal to the split 120 that is parallel to the frontal plane 152 at the split 120. The portion of the catheter assembly 100 that is between the frontal plane 152 at the split 120 and the frontal plane 154 distal to the split 120 (designated 156 in FIG. 1A) is referred to herein as the "junction portion" of the catheter assembly and resides within the previously defined dual or split portion of the catheter assembly. The junction portion is considered to be the portion of the catheter assembly distal to but near the junction, and this can be defined as a variety of different distances. The junction portion 156 may be defined as the portion from the split to 5 mm distal of the split in some embodiments. The junction portion 156 may be defined as the portion from the split to 10 mm distal of the split in some embodiments. The junction portion 156 may be defined as the portion from the split to 20 mm distal of the split in some embodiments. As will be explained further below, in addition to being defined as a specific distance along the catheter distal from the split, the junction portion 156 may alternatively be defined functionally as a clot forming risk region distal to the split, or as another alternative structurally as an area of overlap or contact between the catheters distal to the split.

Also defined in FIG. 1 is a gap distance 162. This gap distance is defined as the perpendicular distance in the transverse plane between the inner surfaces of the split wall that face each other distal to the split 120 at the location of the frontal plane 154 that defines the distal extent of the junction portion 156. This gap distance will vary with varying angles of separation of the two lumens distal to the split 120.

FIG. 1C schematically illustrates a cross section of the merged portion of catheter body 110 formed as a single double-lumen catheter portion in which lumens 115 and 117 are abutting and sharing a single separating wall; nevertheless this should be considered one of many alternative exemplary configurations; other possible configurations may include different multiple-lumen shapes or any connection or adjunction (e.g., by welding, gluing or otherwise) along a surface, a line and/or points of contact between first catheter 111 and second catheter 113. Optionally and alternatively, the two catheters are not merged and/or are detachably connectable along a length thereof. The embodiment of FIG. 1 as illustrated by FIG. 1C is known as a "double-D" type catheter assembly. Split or dual tip double-D type catheter assemblies are characterized by two approximately semi-circular lumens with adjacent flat sides defined by a centrally positioned substantially linear wall. The outer circumference of the catheter assembly in the merged portion is typically of approximately circular cross section. As shown in FIG. 1, when formed into a split or dual tip, the two lumens are separated by cutting through and along the shared centrally positioned substantially linear wall. The direction of the splitting line is therefore the same as the direction of the extent of the central wall in the junction portion of the catheter assembly. For double-D type catheters, the angle of separation of the two lumens may be a dihedral angle formed at the junction or splitting line 120 by the intersection of the planes defined by the inner planar surfaces of the two lumens in the junction portion 156. The double-D type split or dual tip catheter is an especially advantageous application of the embodiments described herein.

First catheter 111 has a first proximal end region 112 which includes a first proximal hub or port 114, and a first distal end region 122 terminating in a first tip 124 which includes a first forward opening 132, such that first lumen 115 extends between first port 114 and first forward opening 132. Likewise, second catheter 113 has a second proximal end region 116 which includes a second proximal hub or port 118, and a second distal end region 126 terminating in a second tip 128 which includes a second forward opening 136, such that second lumen 117 extends between second port 118 and second forward opening 136. Catheter assembly 100 may include connection tubing that has clamps on them (such as clamp 172 on first catheter 111 tubing and clamp 174 on second catheter 113 tubing), and it may have a cuff 160, optionally from Dacron or other materials, for in-growth purpose.

Catheter assembly 100 is configured to connect with a hemodialysis machine (connection can be facilitated via ports 114 and 118) such that one catheter can be set to deliver oxygenated blood into the cardiovascular system and the other catheter can be set to draw blood therefrom, while occasionally the blood circulation may be reversed between these two catheters. First lumen 115 and second lumen 117 are independent from each other for facilitating simultaneous flow in opposite directions.

First catheter 111 and second catheter 113 split from a unitary form of body 110 at splitting line 120 such that their walls are longitudinally split from each other relatively to a median plane in a Cartesian coordinate system, which optionally includes and/or extends from longitudinal axis 135. Optionally and alternatively, both walls are split relatively to longitudinal axis 135 and not relatively to the median plane. Optionally, first distal end region 122 and second distal end region 126 extend substantially the same from the splitting line 120 such that second tip 128 is in apposition to first tip 124. Unlike nonsymmetrical split-tip dialysis catheters having distal end regions of different lengths, symmetrical hemodialysis catheter like catheter assembly 100 are believed to diminish the degree of unwanted dialyzed blood recirculation as may possibly occur between an upstream positioned lumen and a downstream positioned lumen.

First distal end region 122 and second distal end region 126 may be substantially pliant to conform (optionally, juxtaposingly) to boundaries of a hosting vessel lumen. Optionally and alternatively, first distal end region 122 and second distal end region 126 are substantially elastic or rigid such that first tip 124 and second tip 128 are provided in a predetermined distance and/or relative positioning upon deployment. In some embodiments, first distal end region 122 and second distal end region 126 are formed in a rotational symmetry by overall size and shape and/or openings size, shape and/or distribution, one with the other, relatively to longitudinal axis 135. Optionally and additionally, first distal end region 122 and second distal end region 126 are distanced similarly about a transverse plane (being orthogonal to the median plane in the same Cartesian coordinate system) and/or optionally distanced similarly about median plane 130.

Catheter assembly 100 includes distal openings for local blood dispersion and collection; all openings are shaped and distributed on distal end regions 122 and 126 while maintaining rotational symmetry around longitudinal axis 135. Preferably and as shown, first distal end region 122 and second distal end region 126 are rotationally symmetric yet asymmetric (i.e., are not mirrored), and, as in this example, optionally inverted, with respect to the median plane, in order to minimize potential unwanted recirculation of dialyzed blood between adjacent openings. First forward opening 132 is shaped such to direct flow passing therethrough in a first course with a first direction 142 (shown in FIG. 1B as an outflow but can be reversed to inflow). Likewise, second forward opening 136 is shaped such to direct flow passing therethrough in a second course being nonintersecting with, and optionally parallel to, the first course yet have a second direction 146 which is opposite to first direction 142, meaning that a stream flowing out of first forward opening 132 in first direction 142 shall travel farthest away from second forward opening 136, and vice versa: a stream flowing out of second forward opening 136 opposite to second direction 146 shall travel farthest away from first forward opening 132. The two flow courses may projected in any orientation in space, as represented in a Cartesian coordinate system, including median, transverse and frontal planes, and may include orthogonal projections (i.e., being different than 0) in at least one of these planes. In some embodiments, both directions 142 and 146 are not directed laterally away from median plane 130 in order to avoid suction of adjacent vascular wall tissue.

Nevertheless, in order to avoid potential flow occlusion in case of choking of any of the forward openings, lateral openings are also provided, situated distally to the forward openings. Therefore, first catheter 111 includes a first lateral opening 134 located at first distal end region 122 proximal to first forward opening 132, and second catheter 113 includes a second lateral opening 138 located at second distal end region 126 proximal to second forward opening 128. First lateral opening 134 is shaped such to direct flow passing therethrough in a third direction 144 which is opposite to first direction 142. Likewise, second lateral opening 138 is shaped such to direct flow passing therethrough in a fourth direction 148 which is opposite to second direction 146.

FIG. 2 schematically illustrates an exemplary dual-tip hemodialysis catheter assembly 200 with partially facing distal openings, in accordance with embodiments of the present invention. Catheter assembly 200 resembles catheter assembly 100 except that openings are shape and oriented such that flow is directing to or from a catheter median plane, at least in part. Catheter assembly 200 includes two partially merged catheters. The first catheter has a first distal end region 222 terminating in a first tip which includes a first forward opening 232 and the second catheter has a second distal end region 226 terminating in a second tip which includes a second forward opening 236. First distal end region 222 and second distal end region 226 extend substantially the same from the splitting line such that second tip 228 is in apposition to first tip 224, and are formed rotationally symmetric by overall size and shape and/or openings size, shape and/or distribution, one with the other, relatively to longitudinal axis 235. Optionally and additionally, first distal end region 222 and second distal end region 226 are distanced similarly about a transverse plane (being orthogonal to the median plane in the same cartesian coordinate system) and/or optionally distanced similarly about the median plane.

Catheter assembly 200 includes distal openings for local blood dispersion and collection; all openings are shaped and distributed on distal end regions 222 and 226 while maintaining rotational symmetry around longitudinal axis 235. First forward opening 232 is shaped such to direct flow passing therethrough in a first direction 242 (shown in FIG. 2 as an outflow but can be reversed to inflow). As shown, first direction 242 is directed towards the median plane and away from the transverse plane, and comprising an orthogonal projection $242_x$ to median plane 230, which is orthogonal both to the transverse plane and the frontal plane in same Cartesian coordinate system. Likewise, second forward opening 236 is shaped such to direct flow passing therethrough in a second direction 246 which is parallel in course yet opposite to first direction 242. The first catheter includes a first lateral opening 234 located at first distal end region 222 proximally to first forward opening 232, and the second catheter includes a second lateral opening 238 located at second distal end region 226 proximally to second forward opening 228. First lateral opening 234 is shaped such to direct flow passing therethrough in a third direction 244 which has same direction about the median plane as first direction 242 yet is in opposite about the transverse plane. Likewise, second lateral opening 238 is shaped such to direct flow passing therethrough in a fourth direction 248 which has same direction about the median plane as second direction 246 yet is in opposite direction about the transverse plane.

Figure 3:
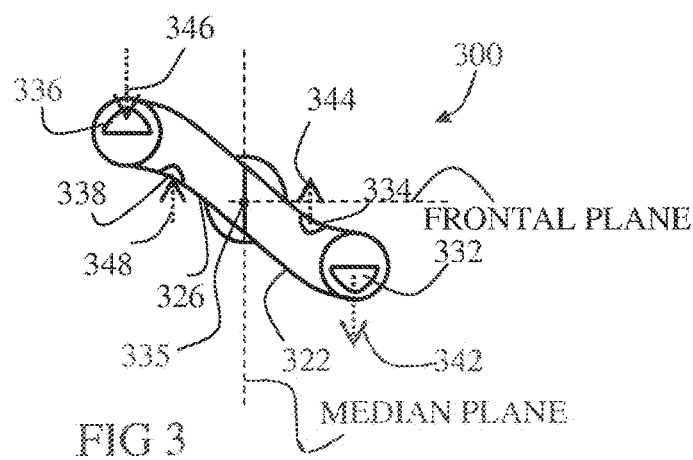
FIG. 3 schematically illustrates an exemplary dual-tip hemodialysis catheter assembly with diverging distal end regions, in accordance with embodiments of the present invention.

FIG. 3 schematically illustrates an exemplary dual-tip hemodialysis catheter assembly 300 with diverging distal end regions, in accordance with embodiments of the present invention. Catheter assembly 300 resembles catheter assembly 100 except that its end regions points to opposite directions with respect to a transverse plane in a Cartesian coordinate system and optionally twisted, at least in part, around a longitudinal axis 335. Catheter assembly 300 includes two partially merged catheters. The first catheter has a first distal end region 322 terminating in a first tip which includes a first forward opening 332 and the second catheter has a second distal end region 326 terminating in a second tip which includes a second forward opening 336. First distal end region 322 and second distal end region 326 extend substantially the same from the splitting line such that second tip 328 is in apposition to first tip 324, and are formed rotationally symmetric by overall size and shape and/or openings size, shape and/or distribution, one with the other, relatively to longitudinal axis 335. Optionally and additionally, first distal end region 322 and second distal end region 326 are distanced similarly about the transverse plane and/or optionally distanced similarly about the median plane.

Catheter assembly 300 includes distal openings for local blood dispersion and collection; all openings are shaped and distributed on distal end regions 322 and 326 while maintaining rotational symmetry around longitudinal axis 335. First forward opening 332 is shaped such to direct flow passing therethrough in a first direction 342 (shown in FIG. 3 as an outflow but can be reversed to inflow). As shown, first direction 342 is directed parallel to plane 330. Likewise, second forward opening 336 is shaped such to direct flow passing therethrough in a second direction 346 which is opposite to first direction 342. The first catheter includes a first lateral opening 334 located at first distal end region 322 proximally to first forward opening 332, and the second catheter includes a second lateral opening 338 located at second distal end region 326 proximally to second forward opening 328. First lateral opening 334 is shaped such to direct flow passing therethrough in a third direction 344 which is opposite to first direction 342. Likewise, second lateral opening 338 is shaped such to direct flow passing therethrough in a fourth direction 348 which is opposite to second direction 346.

Figure 4B:
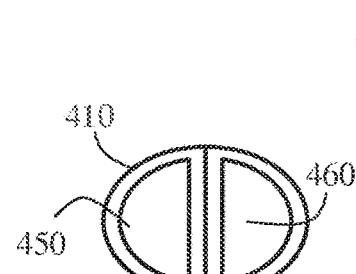
FIGS. 4A-B schematically illustrate an exemplary dual-tip hemodialysis catheter deployed in a blood vessel, in accordance with embodiments of the present invention.
Figure 4A:
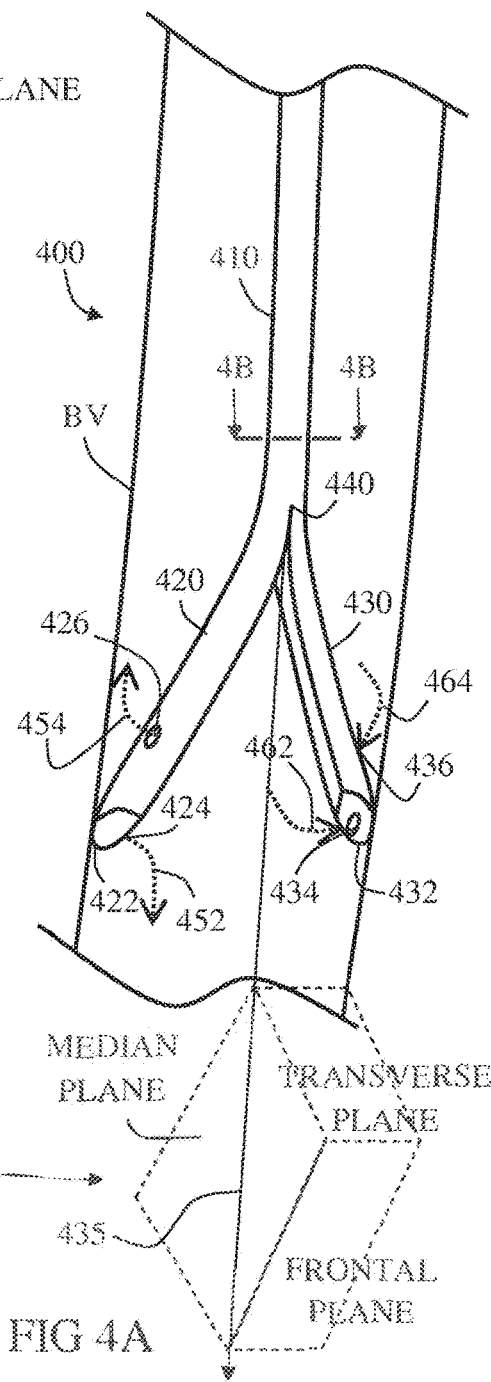

Reference is now made to FIGS. 4A-B which schematically illustrate an exemplary dual-tip hemodialysis catheter 400 deployed in a blood vessel BV, in accordance with embodiments of the present invention. The blood vessel BV may be a large vein, optionally the superior vena cava or the right atrium. Catheter 400 includes an elongated body 410 which extends along a longitudinal axis 435 beginning with a unitary oval cross section and splitting at a junction 440 into a first distal end region 420 terminating in a first tip 422, and a second distal end region 430 terminating in a second tip 432. Elongated body 410 encloses a first lumen 450 extending between a first proximal port (not shown) and first tip 422, and a second lumen 460 extending between a second proximal port (not shown) and second tip 432. Lumens 450 and 460 are isolated one with the other such that fluids passing in one lumen will not communicate with the other lumen. Optionally, the lumens are formed similarly to a double-D formation in which a septum divides first lumen 450 and second lumen 460 along the elongated body length.

In some embodiments, catheter 400 is introduced into blood vessel BV covered with a sheath, optionally a peel-away sheath, which is then withdrawn fully or partially from catheter 400 and/or blood vessel BV, allowing first distal end region 420 and second distal end region 430 to separate one from each other and shift laterally with respect to longitudinal axis 435 up to a predetermined form. Preferably, first distal end region 420 and second distal end region 430 are formed in rotational symmetry one with the other relative to longitudinal axis 435. Optionally, first distal end region 420 and second distal end region 430 maintain at least some elastic properties and therefore tend to shift to their rotationally symmetric formation, at least when not stressed to a different formation.

Preferably, first distal end region 420 and the second end region 430 comprise a plurality of openings distributed and shaped in accordance with the rotational symmetry. The openings are opened to correlating lumen or lumens of the catheter and provide direct fluid communication between the lumen(s) and outside surroundings in blood vessel VB. Each of the first distal end region 420 and the second distal end region 430 comprising at least two openings shaped to direct flow passing therethrough in different directions.

First distal end region 420 comprising a first forward opening 424 located at first tip 422 and second distal end region 430 comprising a second forward opening 434 located at second tip 432. First forward opening 424 is shaped such to direct flow passing therethrough in a first course 452 having a first direction and second forward opening 434 is shaped such to direct flow passing therethrough in a second course 462 nonintersecting with the first course 452. First distal end region 420 also includes a first lateral opening 426 located proximally to first forward opening 424 and shaped such to direct flow passing therethrough in a third course 452 away from the first direction. Second distal end region 430 includes a second lateral opening 436 located proximally to second forward opening 434 and shaped such to direct flow passing therethrough in a fourth course 464, optionally in or towards the first direction, or optionally vertically to the first direction.

In some embodiments, catheter split is relative to a median plane in a Cartesian coordinate system, which is optionally parallel to longitudinal axis 435. In some embodiments, first course 452 and/or second course 462 and/or third course 454 and/or fourth course 464 has an orthogonal projection parallel to the median plane. Optionally, additionally or alternatively, first course 452 and/or second course 462 and/or third course 454 and/or fourth course 464 has an orthogonal projection parallel to a transverse plane orthogonal to the median plane in the Cartesian coordinate system. Optionally, alternatively or additionally, first course 452 and/or second course 462 and/or third course 454 and/or fourth course 464 has an orthogonal projection parallel to a frontal plane orthogonal to the median plane in the Cartesian coordinate system.

A known problem of catheter clotting in split-tip type catheters is at least partially caused by clot formation at the junction portion (i.e., splitting point/line/area) between the distal end regions. This point sees slow or low blood flow and thus, according to "Virchov's triad", is more likely to accommodate thrombosis formation. In some embodiments, dual tip dialysis catheters according to the present disclosures area are shaped such that, at a proper deployment in the body lumen, substantially no gap is formed in the junction portion. Optionally, dual-tip catheters according to the present disclosures are configured to undergo a scissor like movement from an aligned (closed) form to a deployed (opened) form. Optionally the catheter, or portion or member thereof, is elastic and becomes stressed when aligned and unstressed when deployed. Catheter aligning may be achieved in many fashions such as by using an external cover (e.g., a peel-away sheath) or an internal mandrel (e.g., guidewire or stylet), both preferably removable following catheter's deploying.

Figure 5:
FIG. 5 shows a commercially available hemodialysis split-tip catheter shortly following removal from a patient's body.

Reference is made to FIG. 5, which shows a commercially available hemodialysis split-tip catheter shortly following removal from a patient's body. The catheter in FIG. 5 is a double-D type split tip catheter that forms a dihedral angle or a "crack" between the inner planar walls of the two tips in the junction region, comprising an intersection line coinciding with the split line. In conventional catheters, the dihedral angle formed by the separating inner planar walls may be 10 to 30 degrees, and produces a crack in the junction region of the catheter. This crack is a region between the two facing surfaces of the catheter where they are separated by an amount sufficient to impede blood flowing past and over the surfaces, causing blood to pool in a no or low flow condition in the crack so as to produce a clotting risk. This clotting risk can be large when the distance between the two surfaces measured transverse to lumen extent (such distance 162 in FIG. 1A) over their facing portions is between 1 and 3 mm for a longitudinal extent of at least 3 mm. The inventor has devised a dual or split tip catheter that does not contain any such crack in its junction region. In one embodiment described further below, this is accomplished by reducing or eliminating the dihedral angle present in conventional split tip catheters. This crack-free catheter therefore poses less of a clotting risk than conventional catheter assemblies such as the one illustrated in FIG. 5.

Reference is made to FIGS. 6A-C which schematically illustrate a catheter assembly 500, comprising a first catheter 510 and a second catheter 530 merged along a length 501. Length 501 comprises and/or follows a longitudinal axis 502. First catheter 510 includes a first proximal end region 512 comprising a first port 514, a first distal end region 516 terminating in a first tip 518, and a first wall 520 defining a first lumen 522 extending longitudinally therethrough between first port 514 and first tip 518. Second catheter 530 includes a second proximal end region 532 comprising a second port 534, a second distal end region 536 terminating in a second tip 538, and a second wall 540 defining a second lumen 542 extending longitudinally therethrough between second port 534 and second tip 538.

Catheter assembly 500 is configured to connect with a hemodialysis machine (connection can be facilitated via ports 514 and 524) such that one catheter can be set to deliver oxygenated blood into the cardiovascular system and the other catheter can be set to draw blood therefrom, while occasionally the blood circulation may be reversed between these two catheters. In some embodiments, first lumen 522 and second lumen 542 are independent one to the other for facilitating simultaneous flow in opposite directions.

In some embodiments, first wall 520 and second wall 540 are longitudinally split from each other relative to a splitting plane 503 at a junction 504 positioned at or proximally to first distal end region 516 and second distal end region 536. Splitting plane 503 may be a median plane of the catheter assembly 500.

In some embodiments, first catheter 510 and/or the second catheter 530 comprises an elastic member or members 560 (or an elastic portion), about junction 504, having a non-stressed form at first distal end region 516 and second distal end region 536 being separated with each other along splitting plane 503 with no gap therebetween adjacent junction 504. By allowing splitting without a gap, the intention is that flow will not be stagnant at the junction and/or formation of thrombosis will be diminished or avoided.

In some embodiments, catheter assembly 500 includes removable aligning means, such as a removable cover 570 (e.g., a peel-away sheath) for aligning first distal end region 516 together with second distal end region 536 to longitudinal axis 502 (as shown in FIG. 6A). In some embodiments, upon removal of the aligning means, first distal end region 516 and second distal end region 536 voluntarily slide against each other, such as in a scissor-like movement, along splitting plane 503, optionally up to arriving at the non-stressed form of elastic member 560 (as shown in FIG. 6C).

Catheter assembly 500 may be of any form and shape of a split or dual tip catheter having symmetry or similarity in shape and/or size or not having symmetry or similarity in shape and/or size of its two distal end regions and/or openings distributed thereon. For demonstrative purposes the following description relates to two distal end portion having similarity and symmetry although it should be recognized that this is not a mandatory possibility as noted above. In some embodiments, second tip 538 and first tip 518 extend to substantially same length from junction 504. Optionally, second tip 538 is in apposition to first tip 518 when first distal end region 516 and second distal end region 536 are aligned. Optionally, second tip 538 is farthest to first tip 518 when elastic member 560 is unstressed.

In some embodiments, first distal end region 516 and second end region 536 are formed in rotational symmetry one with the other relative to longitudinal axis 502 and comprising a plurality of openings distributed and shaped in accordance with the rotational symmetry. In some embodiments, each of the first distal end region 516 and the second distal end region 536 comprises at least two openings shaped to direct flow passing therethrough in different directions. In some embodiments, first distal end region 516 comprises a first forward opening 524 located adjacent first tip 518 and second distal end region 536 comprises a second forward opening 544 located adjacent second tip 538. In some embodiments, first forward opening 524 is shaped such to direct flow passing therethrough in a first course 526 having a first direction. In some embodiments, second forward opening 544 is shaped such to direct flow passing therethrough in a second course 546. In some embodiments, forward openings 524 and 544 are designed such that second course 546 is nonintersecting with first course 524.

In some embodiments, first distal end region 516 comprises a first lateral opening 528 located proximally to first forward opening 524, and second distal end region 536 comprises a second lateral opening 548 located proximally to second forward opening 544. In some embodiments, first lateral opening 528 is shaped such to direct flow passing therethrough in a third course 529 directed away from the first direction (of first course 526). In some embodiments, second lateral opening 548 is shaped such to direct flow passing therethrough in a fourth course 549 directed in or towards the first direction (of first course 526). Optionally, additionally or alternatively, first lateral opening 528 is shaped such to direct flow passing therethrough vertically to the first direction of first course 526.

In some embodiments, first course 526 has an orthogonal projection parallel to splitting plane 503. Optionally, additionally or alternatively, first course 526 has an orthogonal projection parallel to a transverse plane—orthogonal to splitting plane 503 (being a median plane)—in same Cartesian coordinate system. Optionally, additionally or alternatively, first course 526 has an orthogonal projection parallel to a frontal plane—orthogonal to splitting plane 503 (being a median plane)—in same Cartesian coordinate system.

FIGS. 7A-D schematically illustrate a hemodialysis catheter 600, comprising an elongated body 610 extendable along an assembly longitudinal axis 602, in accordance with embodiments of the present invention. In some embodiments, elongated body 610 splits longitudinally into a first distal end region 612, having a longitudinal axis 637 terminating in a first tip 614 and a second distal end region 616, having a longitudinal axis 639, terminating in a second tip 618, relative to a splitting plane 603, at a split 604. In some embodiments, elongated body 610 encloses a first lumen extending 620 between a first proximal port 622 and first tip 614, and a second lumen 624 extending between a second proximal port 626 and second tip 618.

A junction portion 656 is between a frontal plane 652 at split 604 and a frontal plane 654 distal to split 604. In this embodiment, the inner planar surfaces open and diverge in a scissors like manner that is generally parallel to the splitting plane (e.g. the median plane of FIG. 1). Therefore, in the junction region 628, the inner planar surfaces of the two lumens remain in contact even though the lumen walls are no longer extending parallel to one another. Unlike the embodiments illustrated in FIGS. 1A-C, FIGS. 7A-D illustrate the catheter 600 that has a crack-free junction 628. For example, FIG. 1B illustrates the gap distance 162 as discussed above, but FIG. 7C illustrates the crack-free junction portion 656, which is approximately triangular when viewed from the side. The crack-free junction 656 may have a gap distance much less than the gap distance 162 (FIG. 1B) in its relaxed position. In conventional catheters, the gap distance 162 may be 1 to 3 mm at some distances between 5 mm and 20 mm from the split. In the catheter assembly of FIG. 7, this gap distance is less than 1 mm at all times in the junction region, and is advantageously less than 0.5 mm, or even more advantageously less than 0.1 mm, or even more advantageously the two planar inner lumen surface are in direct contact over all their facing surface in region 628.

It can also be seen in the end on view of FIG. 7C that the dihedral angle of conventional catheters is greatly reduced or eliminated. Preferably, the dihedral angle of the catheter of FIG. 7C is less than 10 degrees, more preferably less than 5 degrees, even more preferably less than 1 degree, and most preferably no dihedral angle is formed at all by the diverging planar inner lumen walls.

Catheter 600 is configured to connect with a hemodialysis machine (connection can be facilitated via ports 622 and 626) such that one catheter can be set to deliver oxygenated blood into the cardiovascular system and the other catheter can be set to draw blood therefrom, while occasionally the blood circulation may be reversed between these two catheters. In some embodiments, first lumen 620 and second lumen 624 are independent one to the other for facilitating simultaneous flow in opposite directions. In some embodiments, a septum 632 divides first lumen 620 and second lumen 624 along a non-splitting length 634 of elongated body 610.

In some embodiments, elongated body 610 comprises the junction portion 628 (of elastic member, for example), about the split 604, having a non-stressed form at first distal end region 612 and second distal end region 614 when they are separated with each other along splitting plane 603, with no gap therebetween at the junction portion 656 (as shown in FIG. 7C). By allowing splitting without a gap, the intention is that flow will not be stagnant at the junction and/or formation of thrombosis will be diminished or avoided.

In some embodiments, hemodialysis catheter 600 comprises or may be provided with removable aligning means such as a removable cover 630 (e.g., a peel-away sheath), as shown in FIG. 7A, for aligning first distal end region 612 together with second distal end region 616 to the assembly longitudinal axis 602. In some embodiments, upon removal of the aligning means, first distal end region 612 and second distal end region 616 can voluntarily slide against each other, such as in a scissor-like movement, along splitting plane 603, optionally up to arriving at the unstressed form of the crack-free junction 628.

Catheter 600 may be of any form and shape of a split or dual tip catheter having symmetry or similarity in shape and/or size or not having symmetry or similarity in shape and/or size of its two distal end regions and/or openings distributed thereon. For demonstrative purposes the following description relates to two distal end portion having similarity and symmetry although it should be recognized that this is not a mandatory possibility as noted above. In some embodiments, second tip 618 and first tip 614 extend to substantially same length from the split 604. Optionally, second tip 618 is in apposition to first tip 614 when first distal end region 612 and second distal end region 616 are aligned. Optionally, second tip 618 is farthest to first tip 614 when elastic 628 is unstressed.

In some embodiments, first distal end region 612 and second distal end region 616 are formed in rotational symmetry one with the other relative to the assembly longitudinal axis 602 and comprising a plurality of openings distributed and shaped in accordance with the rotational symmetry. In some embodiments, each of the first distal end region 612 and the second distal end region 616 comprises at least two openings shaped to direct flow passing therethrough, in different directions. In some embodiments, first distal end region 612 comprises a first forward opening 636 located adjacent first tip 614 and second distal end region 616 comprises a second forward opening 638 located adjacent second tip 618. In some embodiments, first forward opening 636 is shaped such to direct flow passing therethrough in a first course 640 having a first direction. In some embodiments, second forward opening 638 is shaped such to direct flow passing therethrough in a second course 642 nonintersecting with first course 640.

In some embodiments, first distal end region 612 comprises a first lateral opening 644 located proximally to first forward opening 636, and second distal end region 616 comprises a second lateral opening 646 located proximally to second forward opening 638. In some embodiments, first lateral opening 644 is shaped such to direct flow passing therethrough in a third course 648, optionally directed away from the first direction. In some embodiments, second lateral opening 646 is shaped such to direct flow passing therethrough in a fourth course 650, optionally directed in or towards the first direction (of first course 640). In some embodiments, first lateral opening 644 is shaped such to direct flow passing therethrough vertically to the first direction (of first course 640). In some embodiments, first course 640 has an orthogonal projection parallel to splitting plane 603. Optionally, splitting plane 603 is a median plane of the hemodialysis catheter. In some embodiments, first course 640 has an orthogonal projection parallel to a transverse plane—orthogonal to splitting plane 603 (being a median plane)—in same Cartesian coordinate system. Optionally additionally or alternatively, first course 640 has an orthogonal projection parallel to a frontal plane—orthogonal to splitting plane 603 (being median plane)—in same Cartesian coordinate system.

Figure 8A:
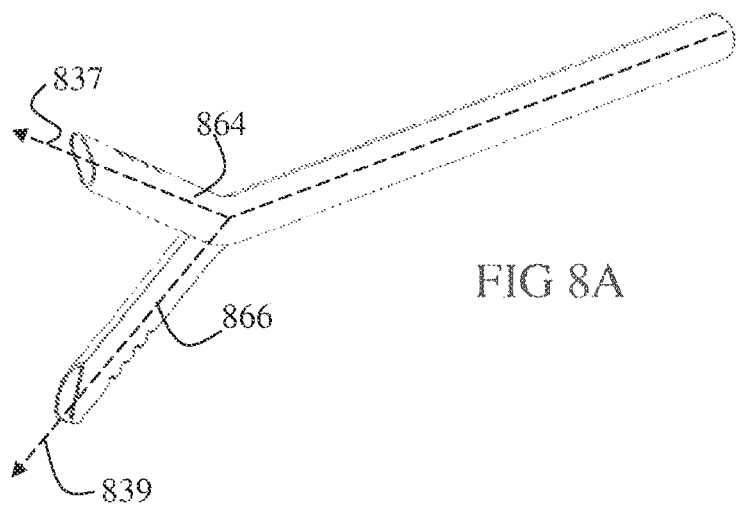
FIGS. 8A-E are perspective views of a hemodialysis catheter in and out of a sheath according to some embodiments.
Figure 8B:
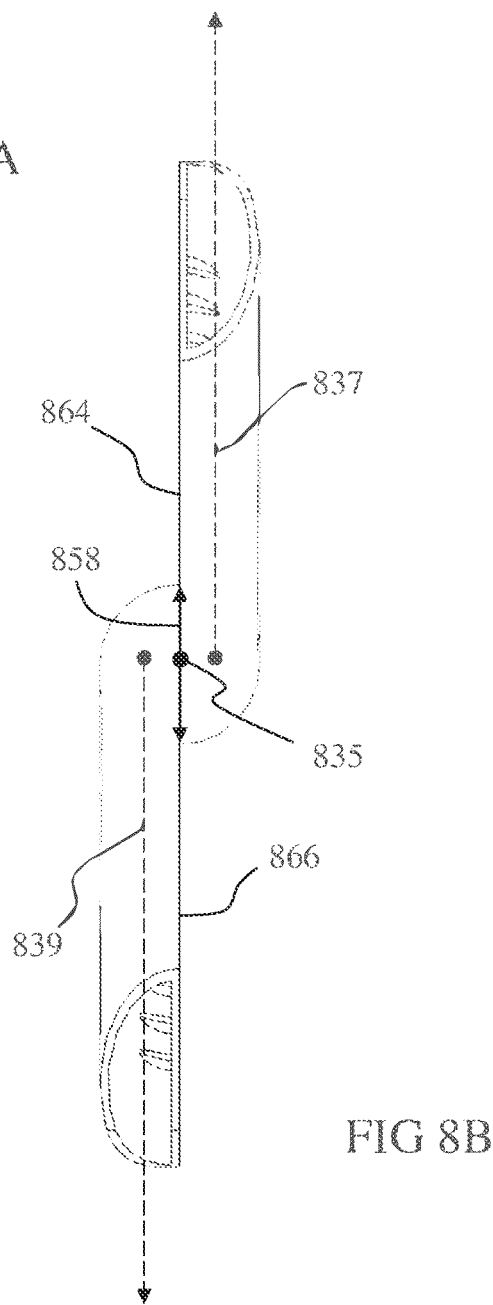

Reference is made to FIGS. 8A-E, which illustrate perspective views of a hemodialysis catheter in and out of a sheath according to some embodiments. FIGS. 8A-B show a catheter assembly with a first lumen, having a longitudinal axis 837 and a first lumen wall 864, and a second lumen, having a longitudinal axis 839 and a second lumen wall 866. The illustrated embodiment has a crack-free junction 835 substantially similar to the crack-free junction 628 (FIG. 7C). The first and second lumen walls 864, 866 may be approximately on the same plane as the median plane 858, which is substantially similar to the splitting plane 603 (FIGS. 7A-D) in its relaxed position, for example. Although the first and second longitudinal axes 837, 839 of the lumens diverge from the transverse plane (as defined above in FIGS. 1B and 1C), they may remain approximately the same distance from the median or splitting plane in the junction region as they diverge. In this embodiment, as contrasted with the configuration of FIG. 1, the lumens diverge mostly or wholly away from the transverse plane (as defined in FIGS. 1B and 1C), rather than mostly or wholly away from the median plane (as defined in FIGS. 1B and 1C). In some embodiments at least one lumen diverges from the transverse plane such that the tip is at least one centimeter from the transverse plane. In some embodiments, both lumens diverge from the median plane less than 5 mm farther from the median plane at their tips. It is to be noted that although the first and second lumen walls 864, 866 may be in contact and on the same median plan 858 at the junction portion 656 (FIG. 7C), the first and second lumen walls 864, 866 distally beyond the junction portion 656 (FIG. 7C) may be free to deviate from the median plane 858 or the splitting plane 603 (FIGS. 7A-D).

Figure 8C:
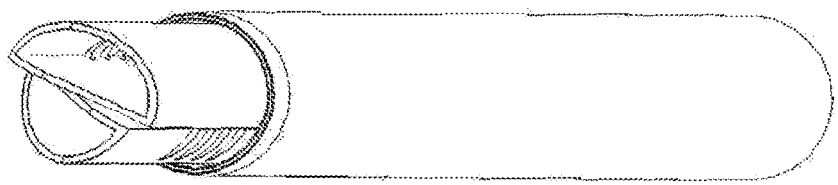
Figure 8D:
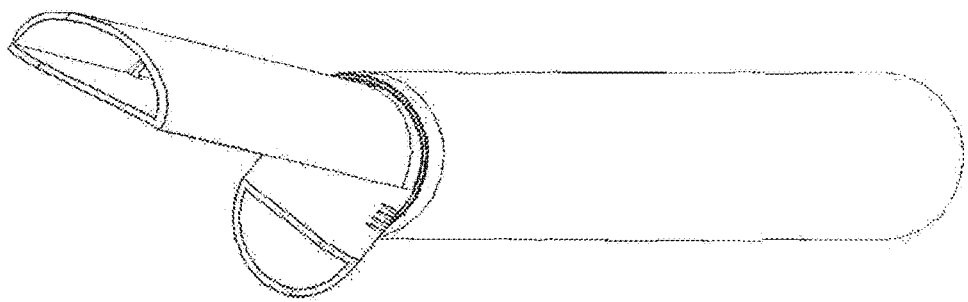
Figure 8E:
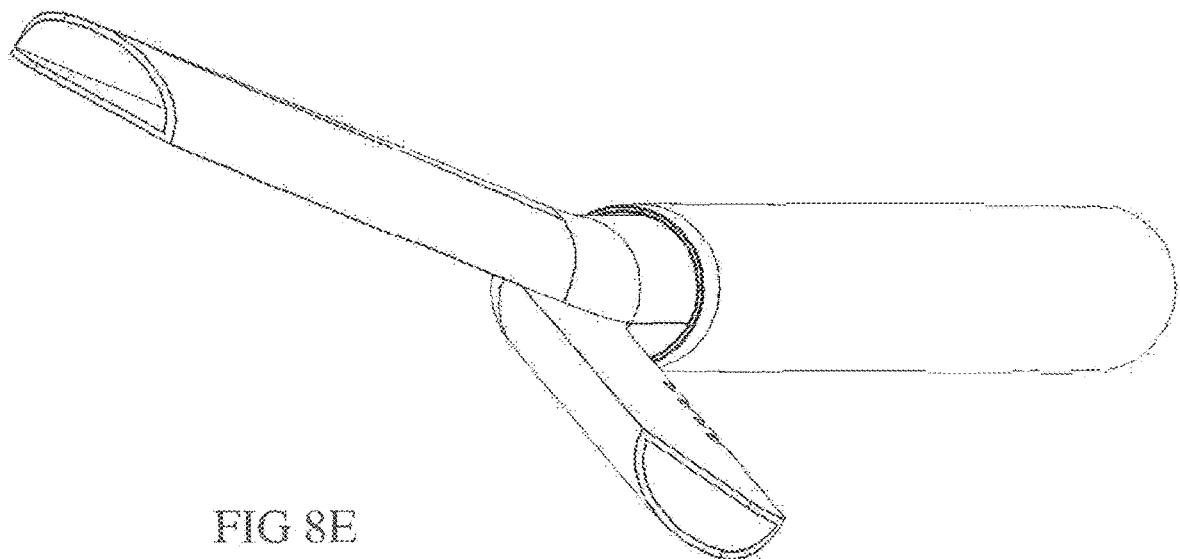

FIGS. 8C-E show a catheter assembly with a removable cover (e.g., a peel-away sheath), substantially similar to the removable cover 630 (FIGS. 7A-B). FIG. 8C illustrates the two distal portions of the catheter assembly substantially aligned with each other as the removable cover holds the two distal portions together. As the two distal portions slide out of the removable cover as illustrated in FIGS. 8D-E, the two distal tips may move away from each other to their relaxed positions in a scissor-like movement.

Figure 9A:
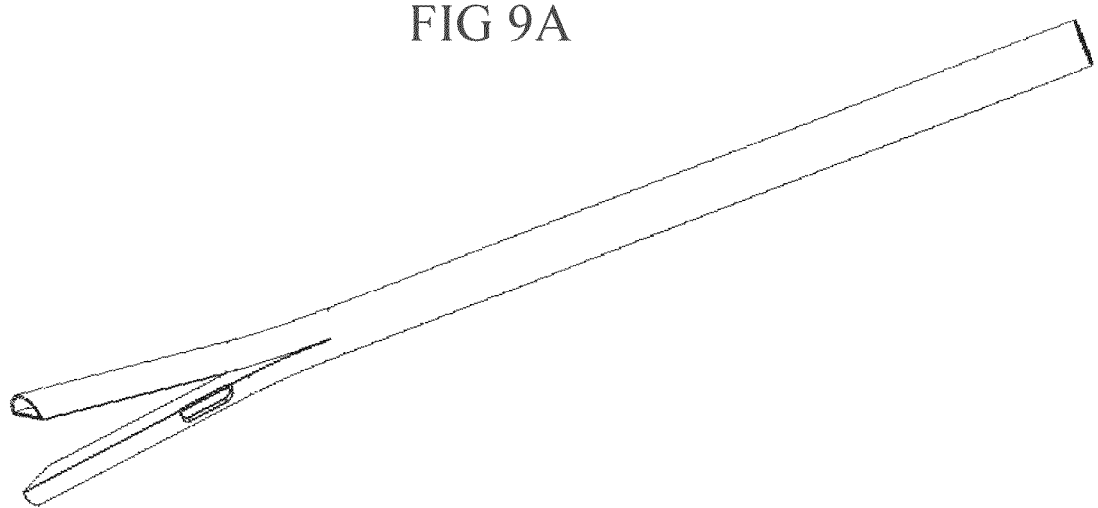
FIGS. 9A-B are perspective views of another embodiment of a hemodialysis catheter according to some embodiments.
Figure 9B:
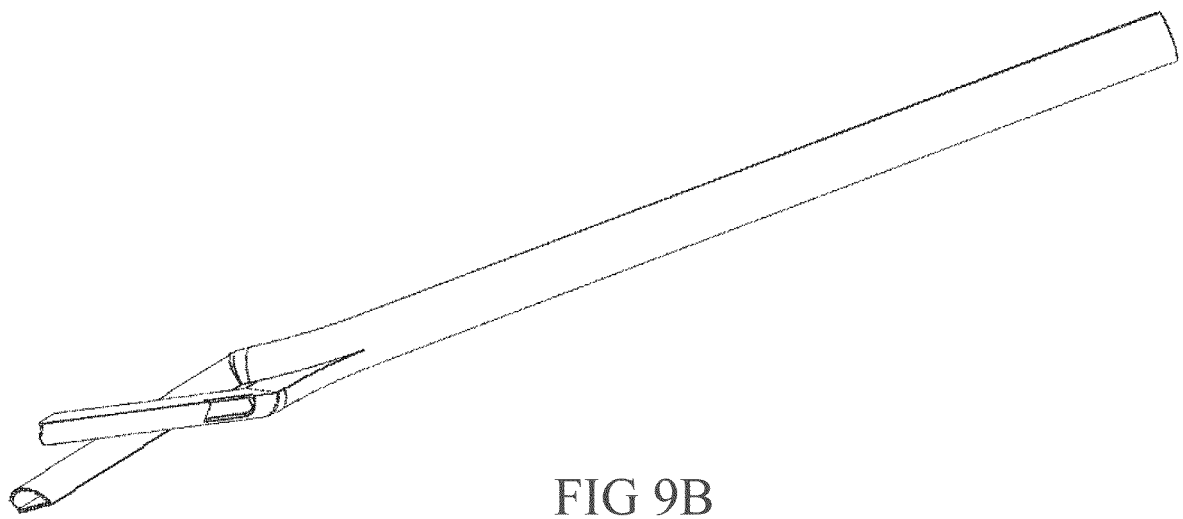

Reference is made to FIGS. 9A-B, which illustrate perspective views of another embodiment of a hemodialysis catheter according to some embodiments. FIG. 9A illustrates a catheter with a crack-free junction substantially similar to the ones illustrated in FIGS. 7A-8E. As discussed in connection with the lumen walls 864, 866 of FIGS. 8A-B, the two distal portions beyond the junction portion 656 (FIG. 7C), may not have the same wall plane. Furthermore, as illustrated in FIG. 9B, the two distal portions beyond the junction portion 656 (FIG. 7C) may not have straight longitudinal axes (such as 837, 839) extending from those of the junction portion 652 (FIG. 7C). The two distal portions beyond the junction portion 656 (FIG. 7C) in FIG. 9B are curved in their relaxed positions so that the two distal portions are twistedly positioned while being longitudinally symmetric by its longitudinal assembly axis (similar to 602 (FIG. 7C)). In another embodiment, the two distal portions may move further away from the median plane providing the catheter assembly to be less twisted than as illustrated in FIG. 9B.

Reference is now made to FIGS. 10A-G which schematically illustrate different scenarios representing possible exemplary steps in a method for forming a dual-tip catheter 1000, in accordance with embodiments of the present invention.

FIG. 10C shows a preformed part 1010 for forming catheter 1000. FIGS. 10A and 10B shows two possible scenarios in a method for forming preformed part 1010. As shown in FIG. 10A, a first preformed member 1001, a second preformed member 1002 and a third preformed member 1003 are collected. First preformed member 1001 encloses a plurality of lumens (in this example—lumens 1004 and 1005) extending therealong and opened at ends 1006 and 1007 thereof. Second preformed member 1002 encloses one lumen 1008 extending therealong and opened at ends 1009 and 1011 thereof. Third preformed member 1003 encloses one lumen 1012 extending therealong and opened at ends 1013 and 1014 thereof.

A shown in FIG. 10B, a first straight mandrel 1015 is inserted through lumen 1004 and lumen 1008, and a second straight mandrel 1016 is inserted through lumen 1005 and lumen 1012, and the three preformed members can be aligned and/or approximated over the first and second straight mandrels 1015 and 1016, as needed. Second preformed member 1002 and third preformed member 1003 are then welded to first preformed member 1001 to form preformed part 1010 in the shape of an elongated body. In some embodiments, lumen 1004 of first preformed member 1001 and lumen 1008 of second preformed member 1002 forms a first passage 1017. In some embodiments, lumen 1005 of first preformed member 1001 and lumen 1012 of third preformed member 1003 forms a second passage 1018.

FIG. 10C shows a finalized version of preformed part 1010 provided for forming catheter 1000. Preformed part 1010 comprises of an elongated body 1019, extendable along a longitudinal axis 1020, and is longitudinally split relative to a splitting plane 1021 at a junction 1022 into a first distal end region 1023 terminating in a first tip 1024 and a second distal end region 1025 terminating in a second tip 1026. Elongated body 1019 encloses first passage 1017 extending along longitudinal axis 1020 and opened at first tip 1024, and second passage 1018 extending along longitudinal axis 1020 and opened at second tip 1026. In some embodiments, elongated body 1019 comprises an elastic portion (or elastic member) across the junction, optionally elongated body 1019 is elastic along most or all its length, optionally radially elastic and/or optionally axially elastic.

In some embodiments, elongated body 1019 is formed of a fluid sealed material whereby first passage 1017 forms a first lumen and second passage 1018 forms a second lumen sealed to the first lumen. Optionally, a septum divides the first lumen and the second lumen along a non-splitting length of elongated body 1019. The fluid sealed material may include polymeric material such as silicone rubber or polyurethane, for example a polycarbonate-based thermoplastic polyurethanes (e.g., Carbothane™)

In some embodiments the preformed members are readily provided with lumens in a final cross section. In other embodiments, the lumens of the preformed members are shaped to a final cross section using the straight mandrels. In some such other embodiments, the first, second and/or third preformed members, 1001, 1002 and 1003, or the welded elongated body 1019, are heated such that first passage 1017 is shaped in accordance with outer boundaries of first straight mandrel 1015, and second passage 1018 is shaped in accordance with outer boundaries of second straight mandrel 1016.

Figure 10D:
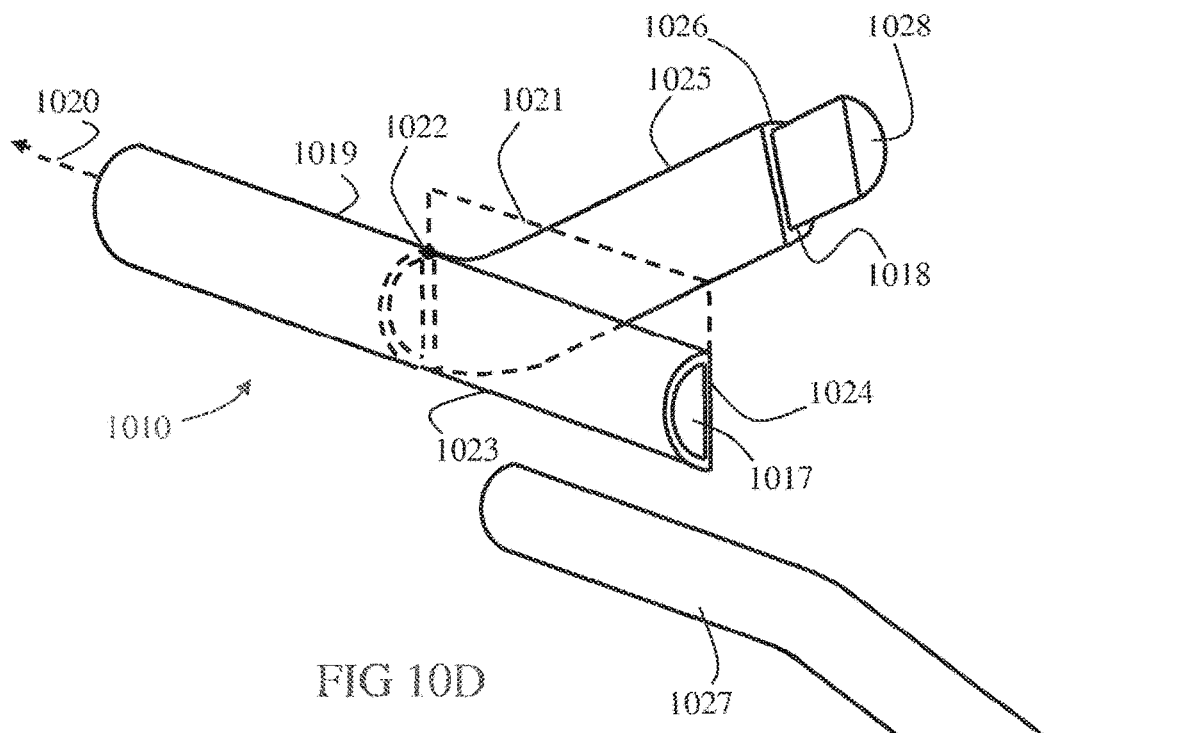
Figure 10E:
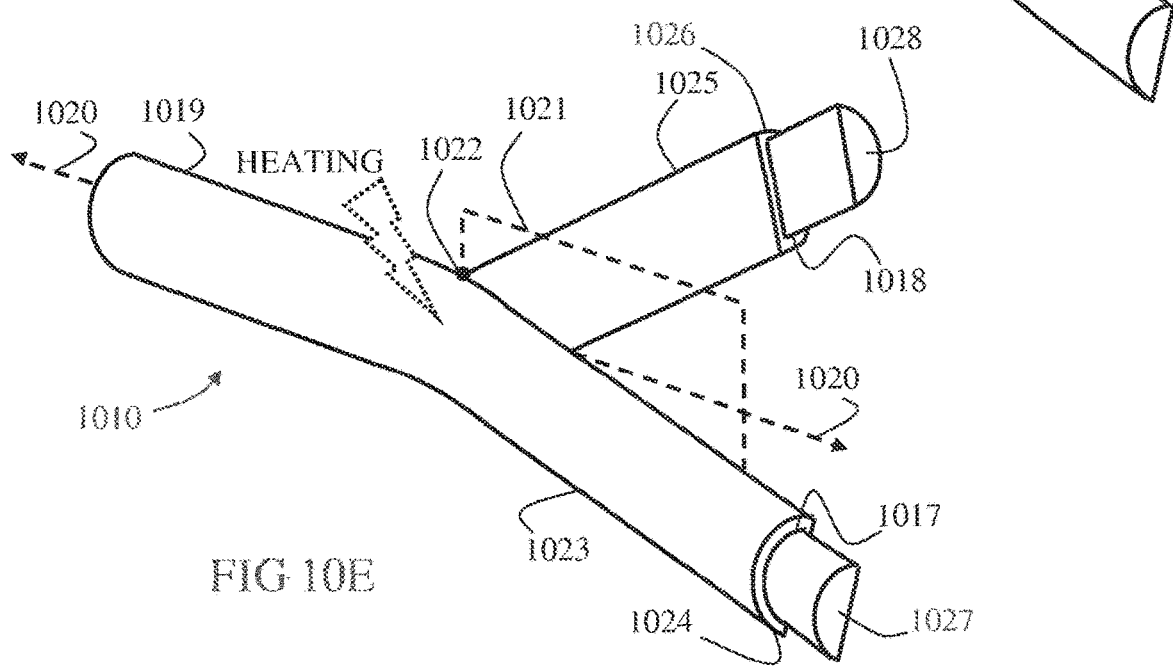

Contoured mandrels are then used in shaping catheter 1000 to its final form. Referring to FIG. 10D, a first contoured mandrel 1027 is inserted in first passage 1017 and a second contoured mandrel 1028 is inserted in second passage 1018, such that first end region 1023 is held in a first contour imposed by first contoured mandrel 1027 (as shown in FIG. 10D) and second end region 1025 is held in a second contour imposed by second contoured mandrel 1028 (shown in FIG. 10E). Elongated body 1019 is then treated for relieving internal stresses (illustrated in FIG. 10E). Optionally, said treating includes at least one of heat treatment, chemical treatment, hardening, and plastic deformation, optionally creating elastic resistivity to a deviation from the non-stressed form. In some embodiments, elongated body 1019 is heated such that first passage 1017 is shaped in accordance with outer boundaries of first contoured mandrel 1027 and second passage 1018 is shaped in accordance with outer boundaries of second contoured mandrel 1028.

Figure 11A:
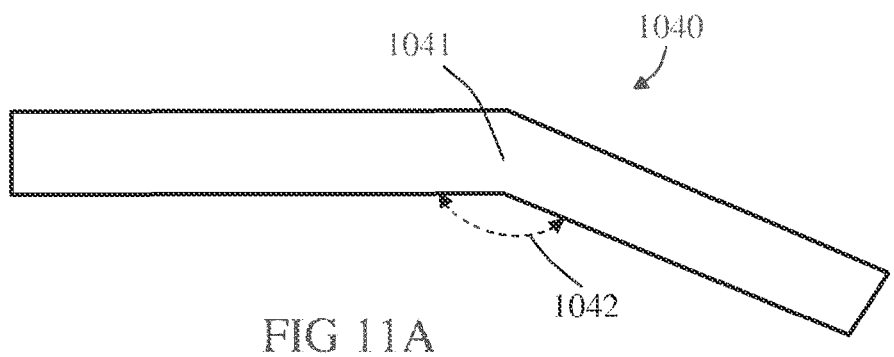
FIGS. 11A-C schematically illustrate side views of exemplary contoured mandrels, in accordance with embodiments of the present invention.
Figure 11B:
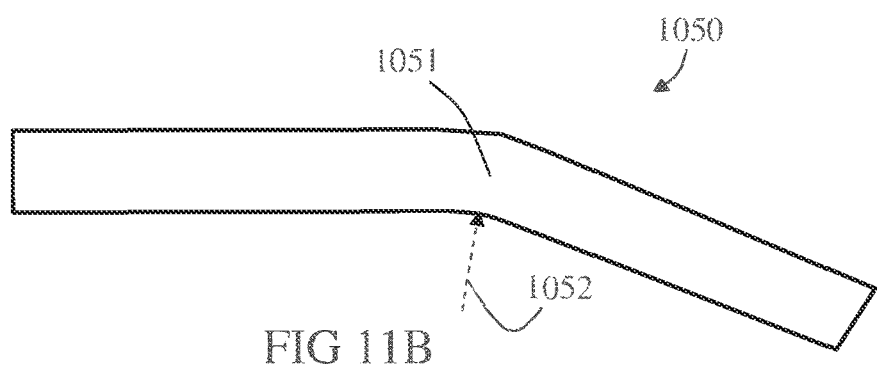
Figure 11C:
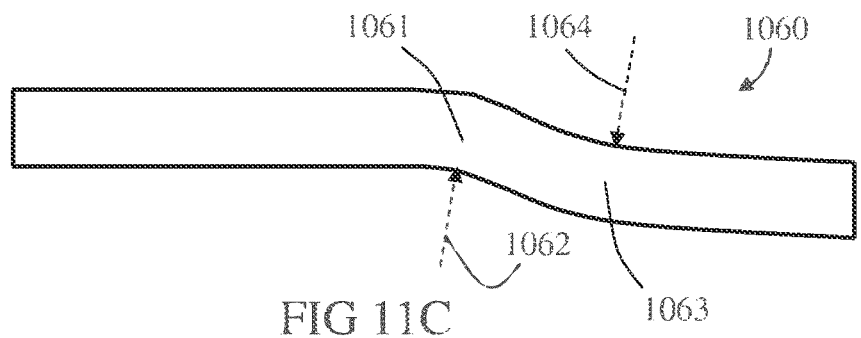

In some embodiments, each of first contoured mandrel 1027 and second contoured mandrel 1028 is fixedly angled or curved along length thereof. FIGS. 11A-C schematically illustrate side views of exemplary contoured mandrels, in accordance with embodiments of the present invention. FIG. 11A shows an angled mandrel 1040 that is fixedly angled at portion 1041 along its length thereby forming angle 1042. FIG. 11B shows a curved mandrel 1050 being fixedly curved in a single portion 1051, along its length, having a radius of curvature 1052. FIG. 11C shows a second curved mandrel 1060 being fixedly curved in a first portion 1061, along its length, having a first radius of curvature 1062, and in a second portion 1063, distal to first portion 1061, having a second radius of curvature 1064. In some embodiments, first contoured mandrel 1027 is congruent or geometrically similar about corresponding angles or curvatures thereof, to second contoured mandrel 1028.

Figure 10F:
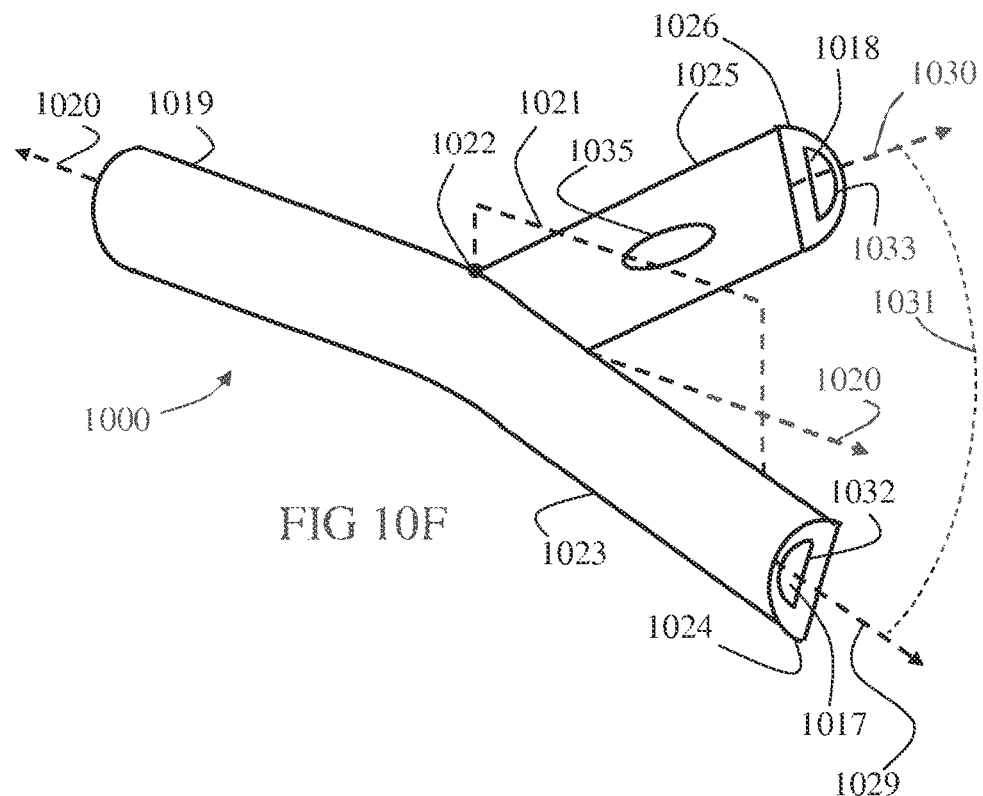

Referring back to FIGS. 10A-G, first contoured mandrel 1027 is then removed from first passage 1017 and second contoured mandrel 1028 is removed from second passage 1018. As shown in FIG. 10F, following removal of the contoured mandrels, elongated body 1019 in its non-stressed form has first end region 1023 and second end region 1025 separated with each other along splitting plane 1021 with no gap therebetween adjacent junction 1022. Elongated body 1019 in its non-stressed form has first tip 1024 pointed towards a first direction 1029 and second tip 1026 pointed towards a second direction 1030 angled to first direction 1029, relative to splitting plane 1021, optionally forming an angle 1031 therebetween with junction 1022 in splitting plane 1021. Angle 1031 may be at least 15°, optionally at least 30°, optionally at least 45°, optionally 45° to 90°.

In some embodiments, first end region 1023 held in the first contour and second end region 1025 held in the second contour form rotational symmetry one with the other relative to longitudinal axis 1020. Also shown in FIG. 10F are openings formed and/or shaped in at least one of the end regions. Optionally, each of the first distal end region 1023 and the second distal end region 1025 comprises at least one opening distributed and shaped in accordance with the rotational symmetry, optionally at least two openings shaped to direct flow passing therethrough in different directions. As shown, first distal end region 1023 comprises a first forward opening 1032 located adjacent to first tip 1024 and a first lateral opening (not shown) located proximally to first forward opening 1032. Second distal end region 1025 comprises a second forward opening 1033 located adjacent to second tip 1026 and a second lateral opening 1035 located proximally to second forward opening 1033. Optionally, first forward opening 1032 is shaped such to direct flow passing therethrough in a first course nonintersecting with a flow in a second course directed by second forward opening 1033.

Figure 10G:
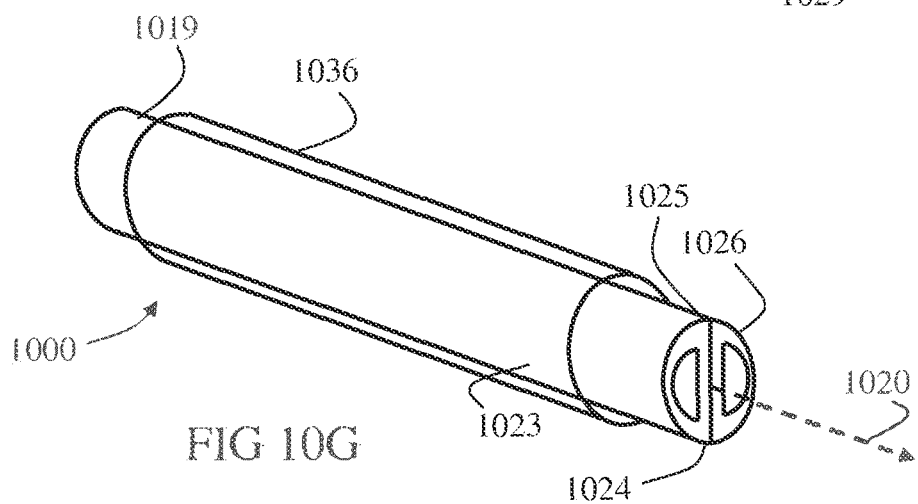

Catheter 1000 is optionally provided to the user with a removable cover, as shown in FIG. 10G. As shown, removable aligning means 1036 are coupled to catheter 1000 for aligning first distal end region 1023 together with second distal end region 1025 to longitudinal axis 1020. Optionally, second tip 1026 is in apposition to first tip 1024 when first distal end region 1023 and second distal end region 1025 are aligned. Upon removal of aligning means 1036, due to elastic characteristics of catheter 1000, first distal end region 1023 and second distal end region 1025 can voluntarily slide against each other, such as in a scissor-like movement, along splitting plane 1021, up to the non-stressed form (shown in FIG. 10F). Optionally, removable aligning means 1036 includes a removable cover such as a peel away sheath.

Reference is made to FIGS. 12A-D which schematically illustrate different scenarios representing possible exemplary steps in another method for forming a dual-tip catheter 1100, in accordance with embodiments of the present invention. FIG. 12A shows a preformed part 1110 provided for forming catheter 1100. Preformed part 1110 is formed of a meshed structure, comprising at least one helically wound filament. The filament is optionally pliable and/or elastic and can be made from metal, polymer, carbon and/or glass, or other. Preformed part 1110 can be provided as a pre-preg (i.e. pre-impregnated) component having a polymeric matrix already present in a partially cured state with the meshed structure. Alternatively, preformed part 1110 may be provided bare and be impregnated and/or coated in a later stage.

Preformed part 1110 comprises of an elongated body 1119, extendable along a longitudinal axis 1120, and is longitudinally split relative to a splitting plane 1121 at a junction 1122 into a first distal end region 1123 terminating in a first tip 1124 and a second distal end region 1125 terminating in a second tip 1126. Elongated body 1119 encloses first passage 1117 extending along longitudinal axis 1120 and opened at first tip 1124, and second passage 1118 extending along longitudinal axis 1120 and opened at second tip 1126. In some embodiments, elongated body 1119 comprises an elastic portion across the junction, optionally elongated body 1119 is elastic along most or all its length, optionally radially elastic and/or optionally axially elastic. Optionally, elastic properties of the entire device are determined according to filaments elasticity and/or mesh design.

Optionally, contoured mandrels are used in shaping catheter 1100 to its final form (mandrels are not shown; final form is shown in FIG. 12B). A first contoured mandrel is inserted in first passage 1117 and a second contoured mandrel is inserted in second passage 1118, such that first end region 1123 is held in a first contour imposed by first contoured mandrel and second end region 1125 is held in a second contour imposed by second contoured mandrel. Elongated body 1119 is then treated for relieving internal stresses. Optionally, said treating includes at least one of heat treatment, chemical treatment, hardening, and plastic deformation, optionally creating elastic resistivity to a deviation from the non-stressed form. In some embodiments, elongated body 1119 is heated such that first passage 1117 is shaped in accordance with outer boundaries of first contoured mandrel and second passage 1118 is shaped in accordance with outer boundaries of second contoured mandrel.

Preformed part 1110 may then be impregnated and/or coated with a polymeric solution, such that elongated body 1119 is formed of a fluid sealed material whereby first passage 1117 forms a first lumen and second passage 1118 forms a second lumen sealed to the first lumen. Optionally, a septum divides the first lumen and the second lumen along a non-splitting length of elongated body 1119. The fluid sealed material may include polymeric material such as silicone rubber or polyurethane, for example a polycarbonate-based thermoplastic polyurethanes (e.g., Carbothane™).

The contoured mandrels can then be removed from first passage 1117 and second passage 1118. As shown in FIG. 12C, following removal of the contoured mandrels, elongated body 1119 in its non-stressed form has first end region 1123 and second end region 1125 separated with each other along splitting plane 1121 with no gap therebetween adjacent junction 1122. Elongated body 1119 in its non-stressed form has first tip 1124 pointed towards a first direction 1129 and second tip 1126 pointed towards a second direction 1130 angled to first direction 1129, relative to splitting plane 1121, optionally forming an angle 1131 therebetween with junction 1122 in splitting plane 1121. Angle 1131 may be at least 15°, optionally at least 30°, optionally at least 45°, optionally 45° to 90°.

In some embodiments, first end region 1123 held in the first contour and second end region 1125 held in the second contour form rotational symmetry one with the other relative to longitudinal axis 1120. Also shown in FIG. 12C are openings formed and/or shaped in at least one of the end regions. Optionally, each of the first distal end region 1123 and the second distal end region 1125 comprises at least one opening distributed and shaped in accordance with the rotational symmetry, optionally at least two openings shaped to direct flow passing therethrough in different directions. As shown, first distal end region 1123 comprises a first forward opening 1132 located adjacent to first tip 1124 and a first lateral opening (not shown) located proximally to first forward opening 1132. Second distal end region 1125 comprises a second forward opening 1133 located adjacent to second tip 1126 and a second lateral opening 1135 located proximally to second forward opening 1133. Optionally, first forward opening 1132 is shaped such to direct flow passing therethrough in a first course nonintersecting with a flow in a second course directed by second forward opening 1133.

Catheter 1100 is optionally provided to the user with a removable cover (e.g., a peel-away sheath), as shown in FIG. 12D. As shown, removable aligning means 1136 are coupled to catheter 1100 for aligning first distal end region 1123 together with second distal end region 1125 to longitudinal axis 1120. Optionally, second tip 1126 is in apposition to first tip 1124 when first distal end region 1123 and second distal end region 1125 are aligned. Upon removal of aligning means 1136, due to elastic characteristics of catheter 1100, first distal end region 1123 and second distal end region 1125 can voluntarily slide against each other, such as in a scissor-like movement, along splitting plane 1121, up to the non-stressed form (shown in FIG. 12C). Optionally, removable aligning means 1136 includes a removable cover such as a peel away sheath.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. An apparatus, comprising an elongated body extending along a longitudinal axis defining a median plane and a transverse plane perpendicular to the median plane in a same Cartesian coordinate system, said elongated body longitudinally splits relative to the median plane at a junction into a first distal end region terminating in a first tip and a second distal end region terminating in a second tip;
    wherein the elongated body encloses a first lumen extending between a first proximal port and the first tip, and a second lumen extending between a second proximal port and the second tip, the first lumen has a first longitudinal lumen axis and a first lumen wall, and the second lumen has a second longitudinal lumen axis and a second lumen wall, wherein, when the first distal end region and the second distal end region are aligned, the first lumen wall and the second lumen wall extend along the median plane, and the transverse plane contains both the first longitudinal lumen axis and the second longitudinal lumen axis;
    wherein the first distal end region and the second distal end region are configured to voluntary separate from each other along the median plane from aligning with each other such that the first longitudinal lumen and the second longitudinal lumen axes diverge from the transverse plane.

2. An apparatus according to claim 1, wherein a gap distance is less than 0.5 mm in a junction portion, the gap distance is defined as the perpendicular distance with respect to the median plane between the first lumen wall and the second lumen wall in the transverse plane, wherein the junction portion is a portion of the elongated body extending at least 5 mm distally to the junction.

3. An apparatus according to claim 1, wherein the elongated body comprises an elastic portion in proximity to the junction, being stressed when the first distal end region and the second distal end region are aligned, and non-stressed when the first distal end region and the second distal end region are separated from each other when the first longitudinal lumen axis and the second longitudinal lumen axis are diverted from the transverse plane.

4. An apparatus according to claim 1, wherein the elongated body comprises facing planar lumen walls, wherein a dihedral angle formed by intersection of planes defined by the facing planar lumen walls is less than 5 degrees.

5. An apparatus according to claim 1, wherein when the first longitudinal lumen axis and the second longitudinal lumen axis diverge from each other, each of the first longitudinal lumen axis and the second longitudinal lumen axis has approximately the same perpendicular distance from the median plane.

6. An apparatus according to claim 1, wherein at least one of the first longitudinal lumen axis and the second longitudinal lumen axis is configured to diverge at least one centimeter away from the transverse plane at the tip of the diverging lumen.

7. An apparatus according to claim 1, wherein the first and second longitudinal lumen axes are configured to diverge less than five millimeters farther away from the median plane at a tip of each diverging lumen.

8. An apparatus according to claim 1, wherein the first distal end region and the second distal end region are configured to voluntarily slide against each other in a scissor-like movement, along the median plane.

9. An apparatus according to claim 1, wherein the first distal end region and the second distal end region are aligned with each other using removable aligning means, wherein the separation of the first distal end region and the second distal end region can occur upon removal of the removable aligning means therefrom.

10. An apparatus according to claim 1, wherein a septum divides the first lumen and the second lumen along a non-splitting length of the elongated body.

11. An apparatus according to claim 1, wherein the second tip is in apposition to the first tip when the first distal end region and the second distal end region are aligned.

12. An apparatus according to claim 1, wherein the first distal end region and the second distal end region are formed in rotational symmetry one with the other relative to the longitudinal axis and comprising a plurality of openings distributed and shaped in accordance with the rotational symmetry.

13. An apparatus according to claim 1, wherein each of the first distal end region and the second distal end region comprises at least two openings shaped to direct flow passing therethrough in different directions.

14. An apparatus according to claim 1, wherein the first distal end region comprises a first forward opening located adjacent to the first tip and the second distal end region comprises a second forward opening located adjacent to the second tip, wherein the first forward opening is shaped to direct flow passing therethrough in a first course having a first direction and wherein the second forward opening is shaped to direct flow passing therethrough in a second course not intersecting with the first course.

15. An apparatus according to claim 14, wherein the first distal end region comprises a first lateral opening located proximally to the first forward opening, and the second distal end region comprises a second lateral opening located proximally to the second forward opening.

16. An apparatus according to claim 1, wherein the first lumen and the second lumen are independent one to the other for facilitating simultaneous flow in opposite directions.

17. An apparatus, comprising an elongated body extendable along a longitudinal axis defining a median plane and a transverse plane in a same Cartesian coordinate system, the elongated body longitudinally split relative to the median plane at a junction into a first distal end region terminating in a first tip and a second distal end region terminating in a second tip;
    wherein the elongated body encloses a first lumen extending between a first proximal port and the first tip, and a second lumen extending between a second proximal port and the second tip, the first lumen has a first lumen longitudinal axis and a first lumen wall, and the second lumen has a second lumen longitudinal axis and a second lumen wall wherein the first lumen wall and the second lumen wall extend along the median plane;
    wherein the elongated body comprises an elastic portion about the junction, having a non-stressed form when the first end region and the second end region are separated from each other along the median plane with no gap therebetween adjacent the junction, such that the first lumen longitudinal axis and the second lumen longitudinal axis diverge from the transverse plane.

18. An apparatus according to claim 17, wherein, upon removal of a removable aligning means aligning the first distal end region together with the second distal end region to the longitudinal axis, the first distal end region and the second distal end region are configured to voluntarily slide against each other, such as in a scissor-like movement, along the median plane, up to the not form of the elastic portion.

19. An apparatus according to claim 18, wherein the removable aligning means includes a removable cover.

20. An apparatus according to claim 17, wherein the second tip is in apposition to the first tip when the first distal end region and the second distal end region are aligned.

21. An apparatus according to claim 17, wherein, when the first lumen longitudinal axis and the second lumen longitudinal axis diverge from each other, each of the first lumen longitudinal axis and the second lumen longitudinal axis remains approximately the same perpendicular distance away from the median plane.

22. An apparatus according to claim 17, formed as a double-D catheter, wherein each of the first lumen and the second lumen is semi-circular, and, the first lumen and the second lumen have adjacent flat sides defined by a centrally positioned linear wall, split to inner planar surfaces diverging parallel to the median plane.

23. A method comprising:
extending the elongated body of the apparatus of claim 1 in a blood vessel, wherein the first distal end region and the second distal end region are aligned with each other using aligning means;
removing the aligning, means thereby allowing the first distal end region and the second distal end region to voluntary separate from each other along the median plane from aligning with each other, such that the first longitudinal lumen axis and the second longitudinal lumen axis diverge from the transverse plane.

24. The method according to claim 23, further comprising:
connecting the first proximal port and the second proximal port to a hemodialysis machine for delivering oxygenated blood into the blood vessel via the first lumen and simultaneously drawing blood from the blood vessel via the second lumen.

* * * * *